US012691299B2

(12) United States Patent
Honold et al.

(10) Patent No.: US 12,691,299 B2
(45) Date of Patent: Jul. 28, 2026

(54) GENERAL LIGHTING WITH PHOTOBIOMODULATION

(71) Applicant: Sunled Life Science B.V., Amsterdam (NL)

(72) Inventors: Jürgen Eduard Honold, Amsterdam (NL); Martijn Jeroen Dekker, Groningen (NL); Michael Krames, Mountain View, CA (US); Marie Anne Van De Haar, Weesp (NL); Charlie Minter, Hilversum (NL)

(73) Assignee: Sunled Life Science B.V., Amsterdam (NL)

( * ) Notice: Subject to any disclaimer, the term of this patent is extended or adjusted under 35 U.S.C. 154(b) by 567 days.

(21) Appl. No.: 17/750,564

(22) Filed: May 23, 2022

(65) Prior Publication Data

US 2022/0288412 A1      Sep. 15, 2022

Related U.S. Application Data

(63) Continuation of application No. PCT/EP2020/083093, filed on Nov. 23, 2020.

(51) Int. Cl.
*A61N 5/06*              (2006.01)

(52) U.S. Cl.
CPC .......... *A61N 5/062* (2013.01); *A61N 5/0622* (2013.01); *A61N 2005/0627* (2013.01); *A61N 2005/0651* (2013.01); *A61N 2005/0663* (2013.01)

(58) Field of Classification Search
CPC ...................................................... A61N 5/06
See application file for complete search history.

(56) References Cited

U.S. PATENT DOCUMENTS

2006/0030908 A1*    2/2006    Powell ................. A61N 5/0616
                                                                        607/88
2010/0277316 A1    11/2010    Schlangen et al.
                    (Continued)

FOREIGN PATENT DOCUMENTS

CN            104190001 A        12/2014
CN            105431201 A         3/2016
                    (Continued)

*Primary Examiner* — Lynsey C Eiseman
(74) *Attorney, Agent, or Firm* — Benjamin D. van der Sman; Hoyng Rokh Monegier B.V.

(57) ABSTRACT

A lighting arrangement for general lighting, comprising a first light source 10 adapted to emit a first light substantially only in a first predetermined spectrum in a range from 615 nm to 690 nm, one or more driver circuits adapted to provide a first pulsed driving current to the first light source for producing the first light pulsing with a first peak radiant power in the first predetermined spectrum sufficient to induce a photo-biomodulation response in a human body, and a second light source adapted to emit a second light, the second light source being capable of emitting at least 250 lumens. The pulse characteristics of the first light are such that no visible flicker or stroboscopic effects can be observed by the human eye in the combined light from the first and second light sources during steady-state operation of the lighting arrangement, and the combined light from the first and second light sources has a combined colour point at a distance less than 8 Standard Deviation Color Matching to a black body line in a CIE x,y chromaticity space, and a first radiant power of the first light in the first predetermined spectrum is at least twice a second radiant power of the second light in the second predetermined spectrum during the pulses of the first driving current.

16 Claims, 23 Drawing Sheets

(56)                    References Cited

U.S. PATENT DOCUMENTS

| | | |
|---|---|---|
| 2013/0147359 A1 | 6/2013 | Chobot |
| 2014/0058483 A1 | 2/2014 | Zao et al. |
| 2014/0228914 A1 | 8/2014 | Van De Ven et al. |
| 2015/0016088 A1 | 1/2015 | Shiraichi et al. |
| 2016/0337569 A1 | 11/2016 | Prabhakar |
| 2016/0366746 A1 | 12/2016 | Van de Ven et al. |
| 2018/0056027 A1 | 3/2018 | Peeters et al. |
| 2020/0269065 A1 | 8/2020 | Broeng et al. |

FOREIGN PATENT DOCUMENTS

| | | | |
|---|---|---|---|
| EP | 2210036 | A1 | 7/2010 |
| JP | 2001025511 | A | 1/2001 |
| JP | 2013171689 | A | 9/2013 |
| JP | 2017006742 | A | 1/2017 |
| JP | 2018511386 | A | 4/2018 |
| JP | 2019505959 | A | 2/2019 |
| JP | 2020507414 | A | 3/2020 |
| JP | 2020529888 | A | 10/2020 |
| WO | 2009049019 | A1 | 4/2009 |
| WO | 2017131715 | A1 | 8/2017 |
| WO | 2018152255 | A1 | 8/2018 |
| WO | 2019/025892 | A1 | 2/2019 |

* cited by examiner

········· Blue LED 450 nm

— · — YAG 2.7

— —CASN 615

———resulting spectrum

Blue LED 450 nm
YAG 2.7
CASN 615
resulting spectrum

........ Blue LED 450 nm

— · — YAG 2.7

— — CASN 615

——— resulting spectrum

GENERAL LIGHTING WITH PHOTOBIOMODULATION

CROSS REFERENCE TO RELATED APPLICATIONS

The application is a continuation of PCT application No. PCT/EP2020/083093, filed on Nov. 23, 2020, which claims priority from European application No. EP19211059.1, filed on Nov. 22, 2019. All of the above-mentioned applications are hereby incorporated by reference in their entireties.

TECHNICAL FIELD

The invention relates generally to lighting, and more particularly to a lighting apparatus, a lighting arrangement, and a method for providing a general lighting apparatus that delivers radiation in a visible spectrum sufficient to induce photo-biomodulation (PBM) response.

BACKGROUND ART

Photobiomodulation (PBM) involves irradiating a living organism at certain energy/power levels to induce biological or biochemical responses. The irradiation may be in the visible spectrum, such as red light, or in the non-visible spectrum, such as near-infrared (NIR). There has been a significant amount of research about the medical benefits of employing PBM therapy to treat physical and psychological symptoms.

However, most of the equipment that administer PBM radiation are specialized devices that are only available at a very limited number of medical facilities. Moreover, these specialized devices are often so complicated that only a team of well-trained physicians, nurses and technicians can use them. These factors greatly limit the spread of the medical benefits of PBM within the general public.

Therefore, there is a need to overcome the abovementioned disadvantages of the currently available apparatuses and methods.

SUMMARY OF THE INVENTION

It would be desirable to provide an apparatus that is easy to use, energy efficient, cost effective and yet emits an amount of radiation in a way that is effective to induce PBM response.

According to a first aspect of the present disclosure, a lighting arrangement for general lighting is provided, comprising a first light source adapted to emit a first light substantially only in a first predetermined spectrum in a range 615-690 nm, one or more driver circuits adapted to provide a first pulsed driving current to the first light source for producing the first light pulsing with a first peak radiant power in the first predetermined spectrum sufficient to induce a photo-biomodulation response in a human body. The lighting arrangement further comprises a second light source adapted to emit a second light, the second light source being capable of emitting at least 250 lumens, preferably at least 1000 lumens, more preferably at least 2000 lumens. The pulse characteristics of the first light are such that no visible flicker can be observed by the human eye in the combined light from the first and second light sources during steady-state operation of the lighting arrangement. The combined light from the first and second light sources has a combined colour point at a distance less than 8 Standard Deviation Color Matching to a black body line in a CIE x,y chromaticity space, and a first radiant power of the first light in the first predetermined spectrum is at least twice a second radiant power of the second light in the second predetermined spectrum during the pulses of the first driving current.

The lighting arrangement is designed to balance several different considerations, aiming to provide white light suitable for general lighting purposes while simultaneously providing pulsed red light at a sufficient optical power density to provoke a PBM response in a user, while avoiding an excessive amount of visible flicker and avoiding too high energy consumption. The lighting arrangement is also preferably designed to reduce the risk of excessive exposure to the red light, and avoids that the optical power in the red light spectrum moves the colour point too much of the combined light from the first and second light sources.

Traditional light sources already emit some radiation in the band that can induce PBM response in humans. For example, the emission spectrum of conventional incandescent bulbs includes a small amount of red and near infrared light, two of the bands that have been associated with the ability to induce a PBM response. However, medical research indicates that the radiation needs to achieve a certain minimum amount of power density (measured in optical power per unit area) and dosage (measured in energy per unit area) within the PBM-inducing light spectrum before the radiation can induce a PBM response in the subject.

The inventor's analysis of research literature in the PBM field revealed that photo-induced biological or biochemical responses can be triggered by sufficient power density, even if only for a short period. Spreading the radiation over time to achieve the same amount of energy with a power density lower than the relevant threshold may induce no or at most limited PBM response. That is, an insufficient power density is unlikely to be remedied by extending the irradiation time.

Driving an incandescent bulb to provide sufficient power density in the PBM-inducing light spectrum would require an excessive amount of electrical power. New solid-state lighting (SSL) technologies such as light-emitting diodes (LEDs) have lower heat emission and a narrower emission band, contributing to a higher energy efficiency. The light sources also allow for a more precisely controlled emission band, enabling efficient power allocation in the desired emission bands, and more importantly, are capable of reacting rapidly to driving and/or control signals. In other words, timing control with SSL devices is much more precise compared to other types of light sources, such as incandescent or halogen bulbs, which, being thermal emitters, have thermal inertia whereas SSL devices allow for nearly instant reaction to control and/or driving signals with negligible delay, making them suitable for rapid pulsing.

Thus, by driving a light source such as an SSL device or LED, with a pulse instead of a constant or nearly constant signal, it is possible to boost the peak radiant power emitted by the light source while consuming the same amount of electric power. In other words, a light source with pulsed emission can achieve a much higher peak radiant power than the same device with continuous wave (CW) emission. To put it differently, the inventor recognized the ability of pulsing a light source to more efficiently utilize the available electrical energy to emit light with the required amount of (short-term) optical power. In other words, the inventor recognized that while narrow-band light sources such as SSL devices allow for concentrating a limited amount of power into only the desired spectrum, pulsing such narrow-band emission devices further allows concentrating the available power into a short duration to enable such devices to emit radiation that exceeds an elevated power threshold. Another advantage of pulsing is that the light source can cool down between the pulses. This may alleviate the thermal budget of the light source and may allow, e.g. the use of a smaller and less costly light source and driver circuit. A more relaxed thermal budget may also reduce the size of the housing that accommodates the light source and the size of any associated cooling device.

A pulsed light source such as an LED may be used in a lighting arrangement for general lighting, such as a lamp designed for general lighting in an office or residence or other indoor space. Applicant's previous patent applications EP 18212476.8 and PCT/EP2019/074984, which are hereby incorporated by reference in their entireties, disclose lighting arrangements incorporating a pulsed light source emitting near infrared light to achieve a PBM response. However, it is also possible to achieve a PBM response using a pulsed light source emitting red light in the visible spectrum, in particular in the range 615-690 nm, optionally in the range 600-700 nm.

Use of red light for generating the PBM effect has the benefit that the red light also contributes to the visible light from the lighting arrangement. For a lighting arrangement designed to provide white light for general lighting, some light in the red part of the spectrum is necessary to compose the white light. At least a portion of the red light component of the white light can thus be used to perform two purposes, saving power and raising the possibility to reduce the number of components of the lighting arrangement and simply its construction.

Such a lighting arrangement may thus include a first light source providing a pulsed red light in the range 615-690 nm (or 600-700 nm) to achieve a PBM response and to provide a portion of the white light, and a second light source providing light to produce a combined white light suitable for general lighting. The first light source may comprise one or more red LEDs, and the second light source may be a conventional white light source comprising, for example, one or more LEDs, a halogen lamp, fluorescent tube or incandescent light bulb. This type of lighting arrangement permits users to enjoy the health benefits derived by the PBM response without requiring any special measures or treatments.

However, the driving of the first light source should be controlled to balance a number of different considerations. These include providing the pulsed red light at a sufficient power density to induce a PBM response while reducing perceptible flicker, reducing the risk of overly high dosage, and avoiding excessive energy consumption. The lighting arrangement will also preferably avoid that the first light source causes the colour point of the combined light (from the first and second light sources) to vary too much from the desired colour point.

Note that pulsing the first light source to provide light to induce PBM responses at appropriate duration and/or period may greatly reduce the chance of overdosing even if the user stays close to the general lighting apparatus for a period much longer than a typical treatment period of 30 or 60 minutes at a specialist center. For example, some medical research suggests that the beneficial biological response peaks at a dosage of about 10 J/cm$^2$, and the PBM response may cease to be beneficial if the dosage exceeds about 35 J/cm$^2$. Thus, if a user is exposed to a power density level of about 8 mW/cm$^2$ for more than about 60 minutes, then it would be hard for the user to receive the peak benefit.

In other words, sufficiently short pulse duration and/or period may provide sufficient power density to induce PBM responses and at the same time deliver an appropriate amount of total energy density (which is power per unit area multiplied by time) over, e.g., 6 hours or more, without overdosing the user. That way, the user may use the lighting apparatus as a general light source without any need to worry about when to switch it off (to prevent overdosage) and yet can still receive the benefit of PBM-inducing radiation.

In an embodiment, the one or more driver circuits of the lighting arrangement is/are adapted to provide a second driving current to the second light source but not to the first light source, wherein the second driving current is a DC current, an AC current, a rectified AC current, or a pulsed current having a pulse frequency of 2 kHz or more.

In an embodiment, the average first radiant power of the first light is 40% or less of a sum of the average first radiant power of the first light and the average second radiant power of the second light. In an embodiment, the first light source has a peak radiant power in a range from 645 nm to 675 nm, preferably at 660 nm.

In an embodiment, the combination of the first light and the second light has an average color point in the CIE XYZ color space or the CIE x,y chromaticity space that has a distance less than 8 SDCM to a black body line in said color space. In this way, the combined light produced by the first and second light sources is white light suitable for general lighting purposes.

In an embodiment, the second light source comprises a multi-phosphor system, for example a two-phosphor system including a green phosphor and a red phosphor. Alternatively, the second light source may comprises a single phosphor system, for example including a green phosphor, the red light being predominantly provided by the first light source.

In an embodiment, a peak emission power or peak radiant power of the first light source enables a received power density in a range 0.4-50 mW/cm$^2$, optionally 1-15 mW/cm$^2$, measured at a common average distance of between about 0.2 and about 5 m from the first light source. The common average distance may optionally be between about 0.5 and about 3 m from the first light source. The common average distance may optionally be about 2 m. The advantageous effects include research-proven PBM responses beneficial to the human body. Such common average distances may also be suitable for many usage scenarios. The term "common average distance" refers to the average distance from all the light emitting elements of the relevant light source, measured in a direction in which the lighting arrangement is designed to provide peak illumination. For example, when the first light source comprises multiple LEDs, the common average distance from the first light source is the average distance from the multiple LEDs measured in a direction in which the first and second light sources are designed to provide peak illumination.

In an embodiment, a peak emission power of the first light source enables a received power density in a range 0.4-50 mW/cm$^2$, optionally 1-15 mW/cm$^2$, measured at a distance from the lighting arrangement where the illuminance of the combined light from the first and second light sources is approximately 500 Lux, where the distance is measured in a direction in which the lighting arrangement is designed to provide peak illumination.

In an embodiment, the first light source emits at least 3,000 J in the first predetermined spectrum within 8 hours.

In an embodiment, the first light source is adapted to deliver a daily dosage (energy per unit area), e.g. over 8 hours, that is sufficient to induce PBM response in a human body, the dosage being measured at a common average distance of between 0.2 m and 5 m from the lighting arrangement, optionally between 0.5 and 3 m from the lighting arrangement. In an embodiment, the first light source is adapted to deliver a daily dosage of 0.01-5 J/cm² e.g. over 8 hours, measured at a common average distance from the lighting arrangement, where the common average distance from the first light source is between 0.2 m and 5 m, optionally between 0.5 and 3 m from the lighting arrangement.

In an embodiment, the first light source is adapted to deliver a daily dosage sufficient to induce PBM response in a human body, and/or a daily dosage of 0.01-5 J/cm² or preferably 0.01-10 J/cm², wherein the dosage is measured at a distance from the lighting arrangement where the illuminance of the combined light from the first and second light sources is approximately 500 Lux, where the distance is measured in a direction in which the lighting arrangement is designed to provide peak illumination.

In an embodiment, the lighting arrangement is adapted to generate visible light from the first and second light sources combined having a luminous flux having a percentage flicker of not more than 40% Percent Flicker, preferably not more than 20%, during steady-state operation. The limited amount of fluctuation in the luminous flux of the light source increases the comfort of the user of the lighting arrangement. In an embodiment, the lighting arrangement may be adapted to generate visible light without perceptible flicker to the human eye during steady-state operation. This lack of perceptible flicker increases user satisfaction with the lighting arrangement. This may be expressed as the visible light from the first and second light sources combined having a luminous flux having a $P_{st}LM$ of less than 1 during steady state operation. $P_{st}LM$ being the measure adapted by the IEC in IEC 61000-4-15 to quantify the perceptibility of flicker at frequencies up to 80 Hz, with a value of 1 being the threshold above which the majority of people perceive the flicker as annoying.

In an embodiment, the lighting arrangement is adapted to generate visible light from the first and second light sources combined having a luminous flux having a Stroboscopic Visibility Measure (SVM) of not more than 1, and preferably not more than 0.9, even more preferably not more than 0.4 during steady state operation. SVM being the measure adapted by the IEC in CIE TN 006:2016 to quantify the visibility of stroboscopic effect at frequencies from 80 Hz up to 2000 Hz, with a value of 1 being the threshold above which the majority of people can perceive the stroboscopic effect. In an embodiment, the lighting arrangement is adapted to generate visible light from the first and second light sources combined having a luminous flux having a Flicker Index of less than 0.1, during steady-state operation. Flicker Index being the measure to quantify the visibility of flicker, taking into account the essential elements of duty cycle and pulse length, at frequencies up to 80 Hz, with a value of 0.1 being the threshold above which most people perceive the flicker as annoying.

In an embodiment, the pulse characteristics of the first light are such that no stroboscopic effects can be observed by the human eye in the combined light from the first and second light sources during steady-state operation of the lighting arrangement.

In an embodiment, the second light source is adapted to emit at least 250 lumens, optionally at least 500 lumens, optionally at least 2000 lumens, or the first and second light sources in combination may emit at least 250 lumens, optionally at least 500 lumens, optionally at least 2000 lumens. In an embodiment, the correlated color temperature of the light from the lighting arrangement may be in the range 1700-6500K, optionally in the range 2400-5500K. In an embodiment, the color rendering index of the light from the lighting arrangement is in the range 80-99 at a correlated color temperature of about 2700K. Such light satisfy requirements for general lighting purposes, such as brightness, light color and color rendering, making the lighting arrangement particularly convenient and acceptable for general lighting. Needless to say, many suitable combinations of the lumens specification, the CCT and the CRI may be possible. In an embodiment, the lighting arrangement is suitable for task lighting, for example for use as a desk lamp or task area lighting.

It is evident that the various embodiments described and explained above are mutually compatible with each other, unless explicitly stated otherwise. As such, the combination of any number of the features from the embodiments is still within the present disclosure. For example, different combinations of exemplary predetermined spectrums, exemplary (peak) emission power levels of the first light source and exemplary brightness of the second light source are clearly within the scope of the present disclosure.

BRIEF DESCRIPTION OF THE DRAWINGS

Embodiments will now be described, by way of example only, with reference to the accompanying schematic drawings in which corresponding reference symbols indicate corresponding parts, and in which.

The figures are intended for illustrative purposes only, and do not serve as restriction of the scope of protection as specified in the claims.

DESCRIPTION OF ILLUSTRATIVE EMBODIMENTS

The following is a description of certain embodiments of the invention, given by way of example only and with reference to the drawings.

Recent advances in medical research have demonstrated that irradiating a living organism with radiation comprising the IR spectrum and/or red light at certain energy/power levels may induce beneficial biological or biochemical responses. Such irradiation is often referred to as photobiomodulation (PBM). Available medical research results on the medical benefits of employing PBM therapy to treat physical and psychological symptoms are rapidly increasing. Some wavelengths that have attracted particular attention include 606, 627, 630, 632.8, 640, 660 and 670 nm (in the red region) and 785, 800, 804, 808, 810, 820, 830, 850, 904, 980 and 1060 nm (in the NIR region). Some spectrums that have attracted particular attention include 645-680 and 800-870 nm.

Figure 1A:
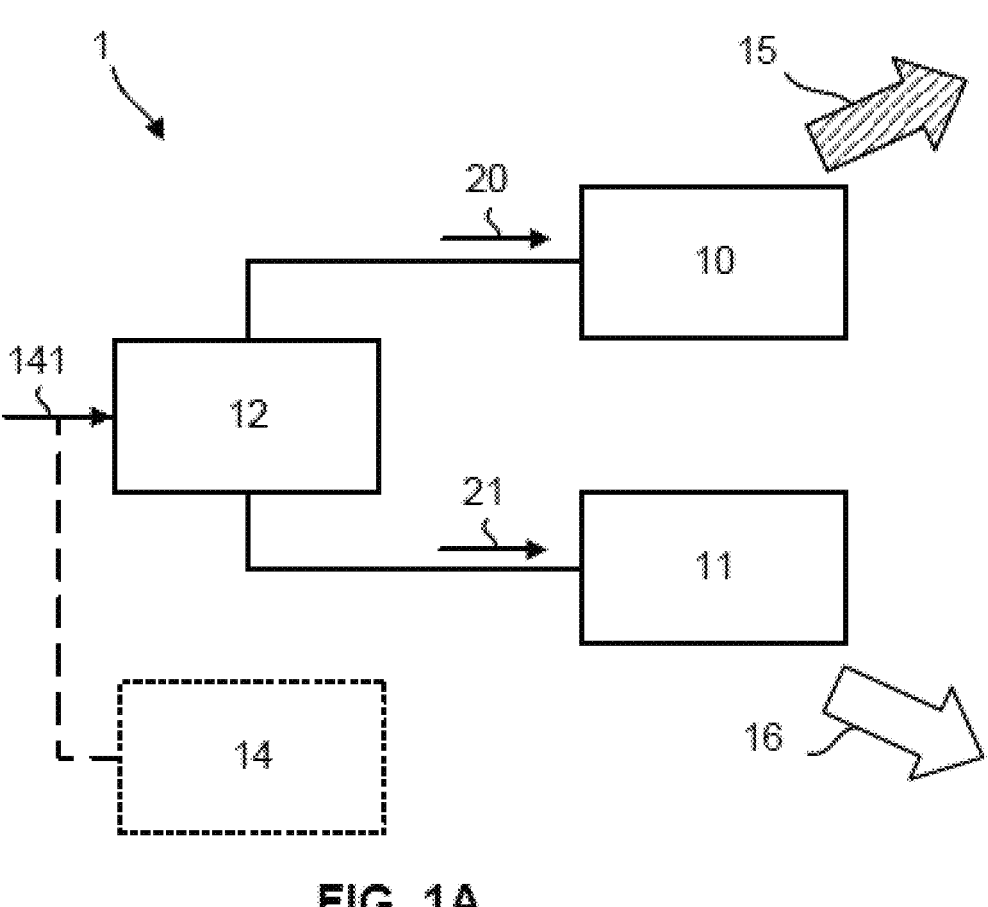
FIG. 1A is a simplified schematic diagram of an embodiment of a lighting arrangement.

FIG. 1A is a simplified block diagram of an embodiment of a lighting arrangement 1, comprising a first light source 10, a second light source 11, and a driver circuit 12. The first light source 10 may comprise one or more solid-state devices, such as LEDs, adapted to emit first light 15 having a first radiant power in a first predetermined spectrum, preferably in a range from 615 nm to 690 nm, or in a range from 600 nm to 700 nm i.e. in the red part of the visible light spectrum. It is possible that first light source 10 additionally emits some light outside of this range. In one embodiment substantially all of the first light 15 falls in the range 650-680 nm. The first light source 10 emits light 15 upon receiving or being energized by a driving signal 20, e.g. an electric current.

The second light source 11 is adapted to second light 16 having a second radiant power in a second predetermined range from 300 nm to 700 nm in the visible part of the light spectrum. The second light 16 is preferably a white light, and preferably has a color point at a distance less than 8 Standard Deviation Colour Matching (SDCM) to a black body line in a CIE XYZ color space and in a CIE x,y chromaticity space (as known in the art, the CIE x,y chromaticity space is a transform of the CIE XYZ color space, the 8 SDCM value being the same in both spaces). The second light source 11 emits light 16 upon receiving or being energized by a driving signal 21, e.g. an electric current.

The second light source 11 is adapted for providing light 16 suitable for general lighting. The term "general lighting" (also referred to as "general illumination") as used herein refers to lighting for the purpose of raising the illumination level to assist human vision in indoor locations in residences, offices, commercial and industrial buildings, and other locations indoor or outdoor where people live or work or are active. It means that when a space is too dark for people to perform desired activities and it is desired to raise the illumination level of the space to enable such activities, the lighting arrangement 1 described herein can be used to provide a sufficient amount of light to achieve the desired increase in the illumination level of that space. For example, a lighting arrangement for general lighting will typically emit white light of at least 250 lumens, for example for task lighting such as a desk lamp, or at least 500 lumens or at least 2000 lumens for lighting larger areas.

Figure 1B:
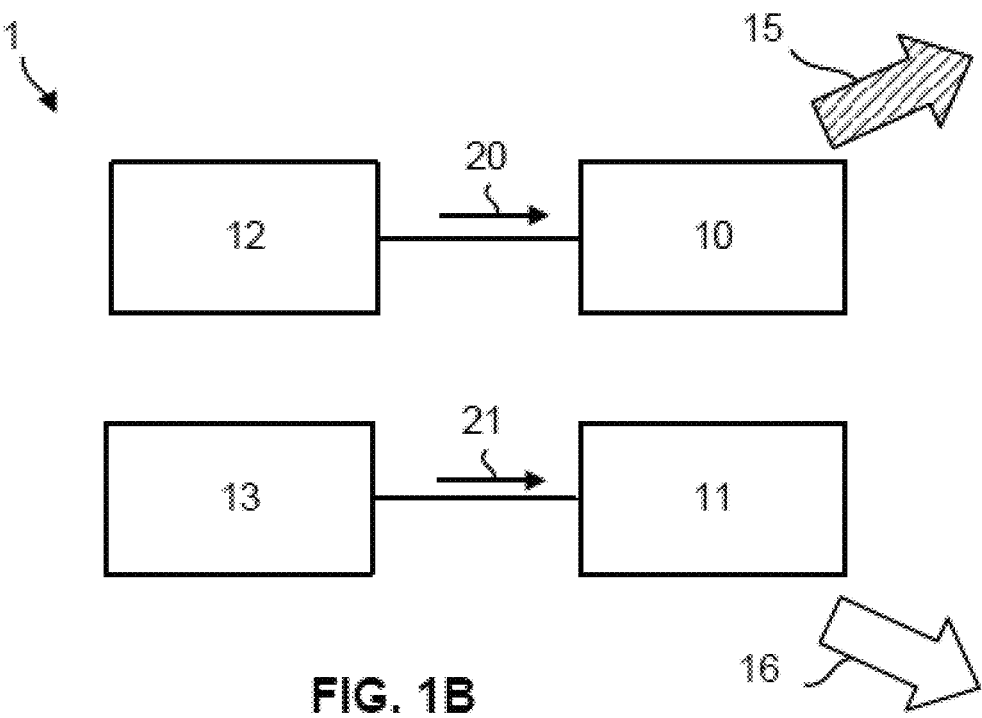
FIG. 1B is a simplified schematic diagram of another embodiment of a lighting arrangement.

The driver circuit 12 may provide driving signals to drive or energize the first light source 10 with first driving current 20 and the second light source 11 with second driving current 21. In an embodiment, the driver circuit 12 provides the first driving current 20 to the first light source 10 and not to the second light source 11, and provides the second driving current 21 to the second light source 11 and not to the first light source 10. Alternatively, two driver circuits 12, 13 may be used, each one separately providing one of the driving currents 20, 21 to one of the light sources 10, 11, as shown in FIG. 1B. Providing separate driver circuits 12, 13 may provide more design flexibility and help reduce interference and cross-talk.

The driver circuit 12 may be arranged to drive the first light source 10 to emit light at different optical powers, e.g.

measured in Watts (W), resulting in different levels of power density (power per unit area) depending on factors such as the radiation pattern of the light source and distance from the light source at which the power density is measured. The power density describes the amount of (optical) power distributed per unit of surface area and may have units such as Watts per meter squared ($W/m^2$) or milli-Watts per centimeter squared ($mW/cm^2$). For example, assuming a light source emits 10 W and is a point source having a uniform spherical distribution pattern, the power density received at a surface two meters from the light source is $10/(4\pi\times2^2)$ equal to about 0.2 $W/m^2$.

The driver circuit 12 is arranged to drive the first light source 10 so that the light 15 is pulsed, the pulses being characterized by a pulse duration (the length of the pulse) and a pulse period (the length of the start of the pulse to the start of the next pulse) and pulse frequency (how often a pulse repeats per second). Note that the light amplitude or intensity emitted by the first light source 10 is not necessarily zero between pulses, but is less than during a pulse, and preferably significantly less, for example where light emission is induced by transients. In an embodiment, the threshold amplitude or intensity that defines a pulse is an amount that is sufficient to induce PBM effects in a living organism, such as a human body.

The shape of the pulse is not particularly limited. In an embodiment, the pulses may have a rectangular shape, but other shapes such as sinusoids, triangles and sawtooth among others are also possible, and a combination of pulses with different shapes is also possible. In an embodiment, the end of a pulse may be defined as the point where the amplitude drops below a predetermined threshold. The predetermined threshold may be about zero or may be non-zero. The predetermined threshold may be defined in relative terms, such as a percentage of the peak amplitude, such as 0.001%, 0.01%, 0.1%, 1%, 5% etc. The predetermined threshold may also be defined in absolute terms. Some pulse shapes may particularly suit certain conditions that depend on the light source, such as the delay or decay effects related to the materials used for the light source (e.g., semiconductor junction or phosphor). A rectangular pulse shape may be advantageous because of the wide variety of available generators for such pulses, such as integrated circuits. A sinusoidal pulse shape may be beneficial where spreading out the radiated optical power is needed.

In an embodiment, the light 15 from the first light source 10 may have a pulse duration in the range of 0.02 ms to 0.5 ms, although other ranges are possible, e.g. 0.01-1 ms. Although shorter pulses are preferred, longer pulses up to 10 ms or longer may be used for some applications.

In an embodiment, the light 15 may have a pulse frequency in the range of 50 Hz to 1000 Hz, although slightly higher ranges are possible, e.g. 1 Hz-2.5 kHz.

The duty cycle describes the ratio between the pulse duration and the period between pulses, and is usually expressed as a percentage. The duty cycle may be calculated by multiplying the pulse duration by the pulse frequency. In an embodiment, the driver circuit 12 is adapted to drive the first light source 10 with an electrical current 20 having a duty cycle of not greater than 10%. Other maximum duty cycle values are also possible, such as 5%, 1%, 0.1%, or 0.01%, and for some applications 20% or higher.

The light 15 from the first light source 10 may have a peak emission power. Emission power, also referred to as radiant power, is usually expressed in Watts (W), which is Joules (J) per second (s). However, in these applications where the pulse is much shorter than 1 second, the peak emission or peak radiant power is usually expressed as if the pulse lasts for a full second. As such, a rectangular 0.1 sec 100 W peak emission power pulse has the same energy flow per unit of time as a rectangular 1 sec 100 W peak emission power pulse, but the total amount of energy in the 0.1 sec pulse is 10 times less. In an embodiment, a peak emission power of the light emitted by the light source (through, e.g., a pulsed driving current) is at least 25 W. In an embodiment, the peak emission power may be at least 50 W, 75 W, 100 W, 150 W, 200 W, 300 W, 400 W or 500 W or more. Constraints to the peak emission power include the available electrical power and the number and physical capabilities of the devices used in the first light source 10. In an embodiment, a peak emission power of the light 15 emitted by the first light source 10 is sufficient to induce beneficial photo-biomodulation (PBM) response in a human body. The radiant power of the first light 15 in the first predetermined spectrum is preferably at least twice the radiant power of the second light 16 in the second predetermined spectrum, during pulsing of the first driving current 21.

The radiant power of light may also be measured in lumens, were a lumen is a unit weighted to the human eye's sensitivity to the light. Note that the radiant power or lumen values for the second light 16, and for the combined light 15, 16, are actually time-averaged power values, i.e. energy per second, rather than the instantaneous peak radiant power during the pulses.

If the light 15 emitted by the first light source 10 is pulsed, then the power density of the light 15 measured at a distance away from the first light source 10 may also vary over time and thus may have peaks and valleys. In other words, if the power density is measured over time and displayed on, e.g., an oscilloscope, then a pulsed signal could be displayed. Peak power density, just as for peak emission power, is the power measured during a pulse, usually expressed as if the pulse lasts a full second. In other words, a peak power density of a 0.1 sec rectangular pulse may be 10 $mW/cm^2$, which leads to a total of 1 $mJ/cm^2$ in the pulse. In an embodiment, the achieved peak power density enabled by the light 15 emitted by the first light source 10 is 0.4-50 $mW/cm^2$ and optionally 1-15 $mW/cm^2$, although other suitable ranges are also possible. The (peak) power density may be measured at a common average distance of between 0.2 m and 5 m from the first light source 10, depending on the usage scenario. Preferably, the first light source 10 may enable the aforementioned ranges of power density at a common average distance of between 0.5 m and 3 m from the first light source 10.

The amount of light emitted may also be expressed in energy (e.g., Joule (J)) or energy density (e.g., $J/cm^2$). In an embodiment, the first light source 15 emits at least 3,000 Joule in the pre-determined spectrum within 8 hours (other energy values and duration values, such as 1, 2, 4 and 6 hours, are also possible).

The total amount of radiation energy received at a given point over a certain period may be expressed in energy per unit area. This amount may be referred to as "fluence" or simply "dose" or "dosage", with $J/cm^2$ being an exemplary unit. In an embodiment, the lighting arrangement 1 is configured so that the first light source 15 delivers a light dosage that is sufficient to induce a PBM response in a human body. Different dosages may be required depending on the type of the PBM response to be induced. In an embodiment, the first light source 15 may be configured to deliver a daily dosage of 0.01-10 $J/cm^2$ measured at a common average distance from the first light source. The common average distance from the first light source may be between 0.2 m and 5 m, depending on the usage scenario, and preferably between 0.5 m and 3 m. Where the first light source is formed by multiple LEDs or other light emitting elements, the common average distance from the first light source refers to the average distance from each of the multiple LEDs or other light emitting elements, measured in a direction in which the lighting arrangement is designed to provide peak illumination.

The first light source 10 may comprise one or more LEDs emitting light predominantly in the red part of the spectrum, preferably in a range from 615 nm to 690 nm, or 600 nm to 700 nm, for example LED(s) based on (non exclusively) Aluminium gallium arsenide (AlGaAs), Gallium arsenide phosphide (GaAsP), Aluminium gallium indium phosphide (AlGaInP) or Gallium(III) phosphide (GaP). Alternatively or additionally, first light source 10 may comprise one or more red emitting phosphor-coated LEDs based on (non exclusively) a combination of a blue emitting semiconductor like Indium gallium nitride (InGaN) and a red light emitting phosphor system, for example non-organic phosphors like CASiN, or other Eu2+ doped systems with a fast rise and fall time. Furthermore, new phosphor systems based on Quantum Dots, or hybrid systems comprising organic and non-organic phosphors may also be used. The enabling factor for alternative phosphor systems is a suitable (relative fast) rise and fall time, to enable pulsing with an acceptable delay of the converted, red light following the excitation and non-excitation.

The second light source 11 is adapted to emit light 16 in the visible spectrum, preferably in the range 300-700 nm, or predominantly in a range excluding the red part f the spectrum, e.g. 300-600 nm. The light 16 may be white light, having a color point at a distance less than 8 Standard Deviation Color Matching to a black body line in a CIE XYZ color space (CIE x,y chromaticity space), or the light 15 and light 16 combined may be white light, having a color point at a distance less than 8 Standard Deviation Color Matching to a black body line in a CIE XYZ color space or CIE x,y chromaticity space. The combined light sources 10 and 11 are preferably adapted to provide light suitable for general lighting purposes as described herein.

In an embodiment, the lighting arrangement 1 comprising the second light source 11 may be adapted to generate visible light 16 having a luminous flux which does not fluctuate by more than 20% or 15% or 10% or 5% or 3% when the light source 11 is in use. Visible light 16 with a limited fluctuation in the luminous flux has less flicker and thus is more suitable for general lighting. In an embodiment, the lighting arrangement 1 may be adapted to generate visible light without perceptible flicker to the human eye, e.g., very low amounts of flicker or only flicker at frequencies too high for a human eye to perceive.

In an embodiment, the second light source 11 may be capable of emitting at least 25 lumens, which is equivalent to about two candles. Such a light source may be useful for home decoration purposes. In an embodiment, the second light source 11 may emit at least 150 lumens, and preferably at least 300 lumens, which is suitable for general lighting purposes in a residence. Other amounts of luminous flux are also possible to suit, e.g., general lighting in an office or a factory environment or outdoors.

In an embodiment, the correlated color temperature (CCT) of the second light source 11 emitting visible light 16 is in the range 1700-6500K, optionally in the range of 2200-5500K, optionally in the range of 2700-4000K. In an embodiment, the color rendering index of the second light source 11 is in the range 80-99 at a correlated color temperature of 2700-3000K. Such light sources are generally more acceptable for general lighting purposes. Needless to say, many suitable combinations of the lumens specification, the CCT and the CRI are possible.

In an embodiment, the second light source 11 may consume an electric power of less than 120 W, optionally less than 80 W, optionally less than 30 W, depending on the power requirements of the usage scenarios for the lighting arrangement 1.

Many types of light sources for general lighting may be used as the second light source 11. For example, the second light source 11 may comprise one or more incandescent bulbs, halogen bulbs, fluorescent tubes, or solid-state devices such as one or more LEDs. In one embodiment, the second light source 11 comprises a standard white light system with CCT in the range 2200-6500K, for example a phosphor-converted white LED (pcLED) comprising a blue or violet pump LED in combination with one or more phosphors covering the light-emitting surface of the pump LED or arranged so that light from the LED enters the phosphors. For example, the phosphors may include a phosphor (such as a YAG phosphor) emitting light predominantly in the green part of the spectrum and/or a phosphor (such as a CASiN phosphor) emitting light predominantly in the red part of the spectrum. Alternatively, the second light source 11 may comprise one or more LEDs with or without one or more phosphors, emitting light predominantly in the green and blue parts of the spectrum and with significantly reduced or no emission in the red part of the spectrum.

The white light system is preferably driven in continuous wave (CW) mode or pulse width modulated (PWM) mode, with a perceptible flicker of less than 10% Percent Flicker, or less than 0.1 Flicker index, or $P_{st}$LM of less than 1. The optical light perception by the human eye in the red part of the spectrum (600-700 nm) is defined by the optical power emitted by the green and/or red phophors (e.g. YAG and CASiN phosphors) in combination with the integral value of the optical power of the pulsed red light 15. The flicker perception induced by the pulsed red light 15 will be very low, particularly in view of the human eye sensitivity at around 670 nm (peak emission).

Preferably the first light source 10 consumes a small fraction of the electrical power consumed by the second light source 11 when the lighting arrangement 1 is in use. The fraction may be 25% or less, 10% or less, or preferably 5% or less. A lower fraction means that the user of the lighting arrangement 1 may obtain the additional benefit of PBM-inducing radiation at a lower marginal power consumption in addition to the benefit of general lighting provided by the second light source 11. The amount of electrical power consumed by the first light source 10 may also be expressed in terms of the fraction of the total electrical power consumption of the first light source 10 and the second light source 11 combined, for example, less than two-thirds, less than one-fifths, or in a range of about 5%-10%.

The first light source 10 is preferably a device which reacts almost instantly, i.e. with a negligible amount of delay, to the first driving current 20, so that the first driving current 20 and the light 15 emitted by the first light source 10 vary over time in a similar or substantially identical way to each other. For example, if modern solid-state device(s) such as LEDs, which can react rapidly to driving current, are used as the first light source 10 and driven by a pulsed driving current 20, then the light 15 emitted by the first light source 10 is also pulsed with similar pulse parameters (such as peak intensity, pulse duration, pulse period/frequency, duty cycle, etc.).

In an embodiment, the second driving current 21 driving the light source 11 is adapted to avoid significant amounts of visible flicker in the light 16. The second driving current 21 generated by driving circuit 12 may be any type of driving current usually used to drive light sources for general lighting, for example, depending on the type of light, a DC current, an AC current, a rectified AC current, or a pulsed current such as a pulse-width modulated current used to achieve dimming control in LED general lighting devices. When the second driving is a pulsed current, the pulse frequency is preferably sufficiently high to avoid significant amounts of visible flicker in the light 16, for example at a frequency of 5 kHz or more. In an embodiment, the second driving current 21 may drive the light source 11 in a continuous-wave (CW) mode or quasi-CW mode. In optical physics and engineering, "continuous wave" or "CW" refers to a light source (such as a SSL device) that produces a continuous output beam, as opposed to a pulsed output beam.

It should be noted that the lighting arrangement 1 may include circuit blocks/elements not explicitly drawn in FIG. 1A or FIG. 1B, such as external power sources, switches, ballasts and ground pins. There may also be additional circuit blocks/elements between the first light source 10 and the driver circuit 12 and/or between the second light source 11 and the driver circuit 12 to achieve various purposes, such as controlling the first and second driving currents 20, 21.

FIGS. 2A-2D schematically present different embodiments of lighting devices incorporating the above-described lighting arrangement 1.

Figure 2A:
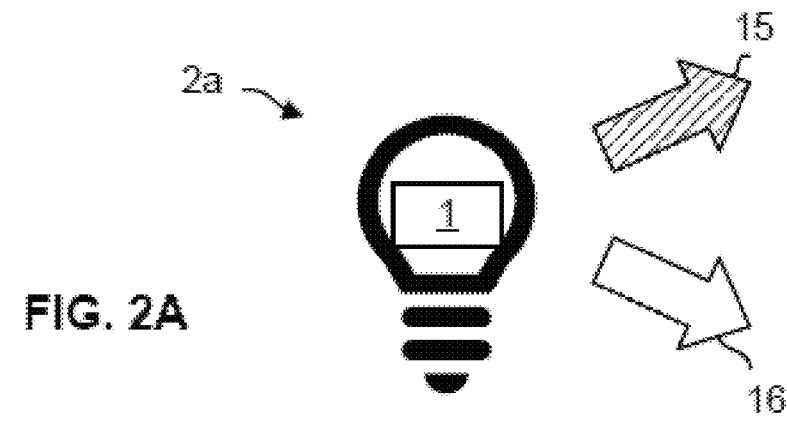
FIG. 2A is a schematic diagram of a light bulb in accordance with an embodiment of the present disclosure.

FIG. 2A illustrates a light bulb 2a comprising a lighting arrangement 1. The light bulb 2a may be a retrofit light bulb that a general consumer would find familiar and easy to use, e.g. an LED lamp designed for operation in a conventional fitting or socket designed for an incandescent light bulb. The first light source 11 in the lighting arrangement 1 may provide sufficient visible white light 16 to make the bulb 2a suitable for general lighting purpose. The visible light 16 may be sufficient in both the senses of quantity (e.g., enough brightness) and quality (e.g. sufficiently low flicker, comfortable color, etc.). After installing and turning on the bulb 2a, the user not only receives visible light 16 for general illumination but is also exposed to the light 15 that may induce beneficial PBM response in the human body.

Figure 2B:
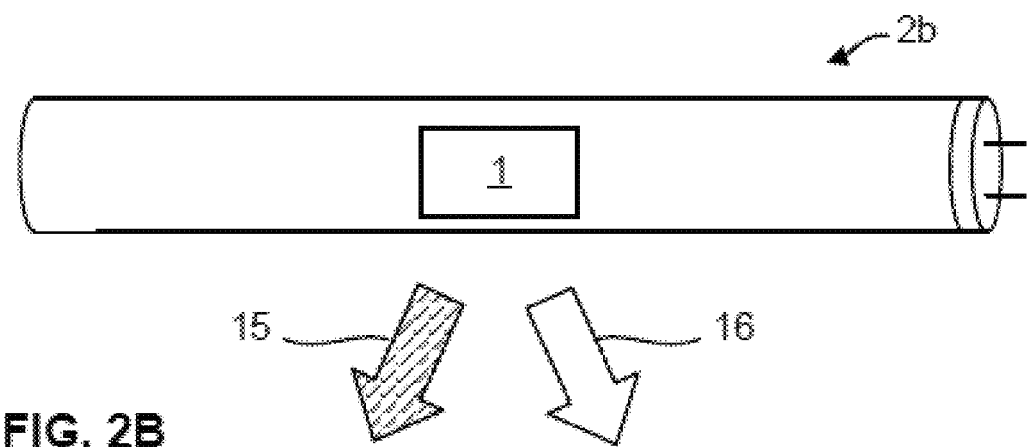
FIG. 2B is a schematic diagram of a light tube in accordance with an embodiment of the present disclosure.

FIG. 2B illustrates a light tube 2b comprising a lighting arrangement 1. The light tube 2b may be a retrofit light tube that a general consumer would find familiar and as easy to use, e.g. an LED lamp configured as a tube adapted to operate in a conventional fluorescent luminaire. Similar to the light bulb 2a, the light tube 2b provides dual functions, general illumination and a beneficial PBM response.

Figure 2C:
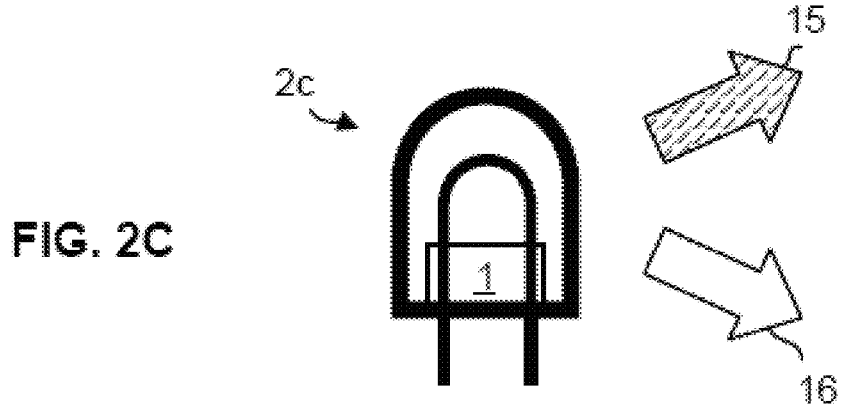
FIG. 2C is a schematic diagram of a lamp in accordance with an embodiment of the present disclosure.

FIG. 2C illustrates a compact lamp 2c comprising a lighting arrangement 1. The lamp 2c may be an off-the-shelf lamp that is adapted to easily fit with existing standard fitting. A general consumer can buy a lamp 2c and use it without the need to call an electrician to adapt the standard fitting, at the same time providing the great versatility and benefits as the lighting arrangement 1 to the user. In an embodiment, the lamp 2c may be customized to fit into a specific fitting.

Figure 2D:
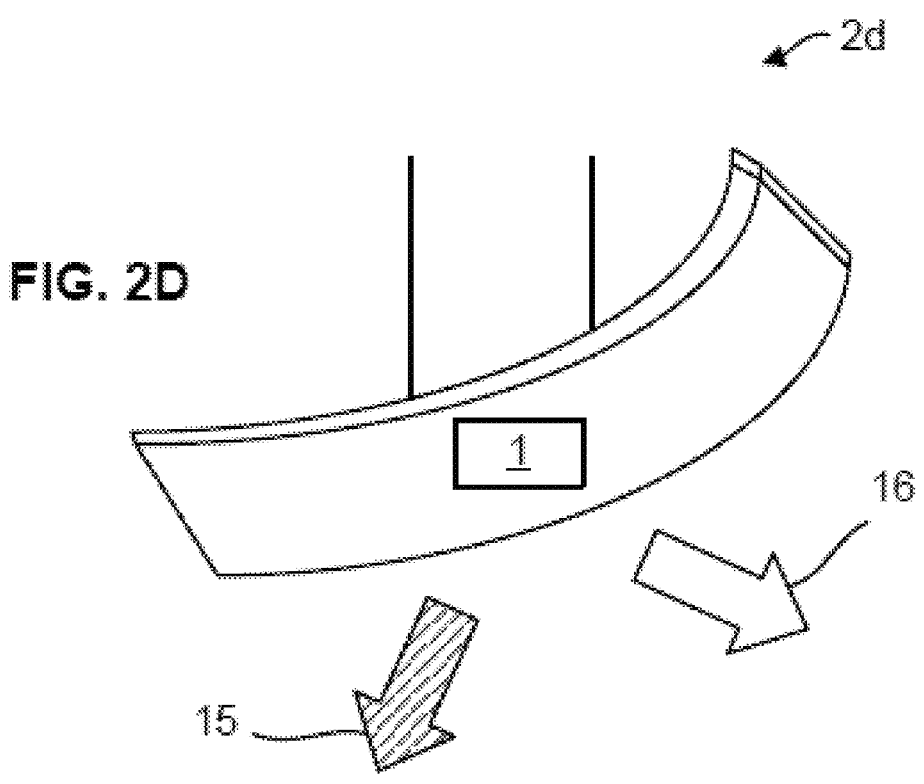
FIG. 2D is a schematic diagram of a luminaire in accordance with an embodiment of the present disclosure.

FIG. 2D illustrates a luminaire 2d comprising a lighting arrangement 1. The luminaire 2d may comprise a light fitting to accommodate the lighting arrangement 1 or a lamp comprising the lighting arrangement 1 and may optionally comprise decorative elements, such as shades, base and/or housing. The luminaire 2d may be used, e.g., in a household or an office environment and may comprise additional light sources to satisfy additional lighting requirements. In an embodiment, the luminaire 2d may be available as off-the-shelf products with all elements of the lighting arrangement 1 already mounted in the luminaire 2d. The user can buy such a luminaire 2d, provide it with electrical power, and directly enjoy the dual benefits of general illumination and medical benefits.

Some elements of the lighting arrangement 1 may be mounted externally to the light bulb 2a, light tube 2b, lamp 2c, or luminaire 2d. For example, the first light source 10 and the second light source 11 may be mounted within the light bulb 2a, light tube 2b, lamp 2c, or luminaire 2d while the driver circuit 12 is placed outside but connected to the light bulb 2a, light tube 2b, lamp 2c, or luminaire 2d. If the first light source 10 and the light source 11 are driven by two driving circuits, one of the driving circuits may be mounted within and the other may be placed outside the light bulb 2a, light tube 2b, lamp 2c, or luminaire 2d. It is also possible to use more than one luminaire with some elements of the lighting arrangement 1 mounted in one luminaire and the other elements of the lighting arrangement 1 mounted in another luminaire. For example, the first light source 10 and the driver circuit 12 may be mounted in one luminaire, and the light source 11 and the driver circuit 13 may be mounted in another luminaire. Although specific embodiments of the lighting arrangement 1 is illustrated in FIGS. 2A-2D, it should be evident that this is not limiting and many other arrangements are possible.

Figure 6:
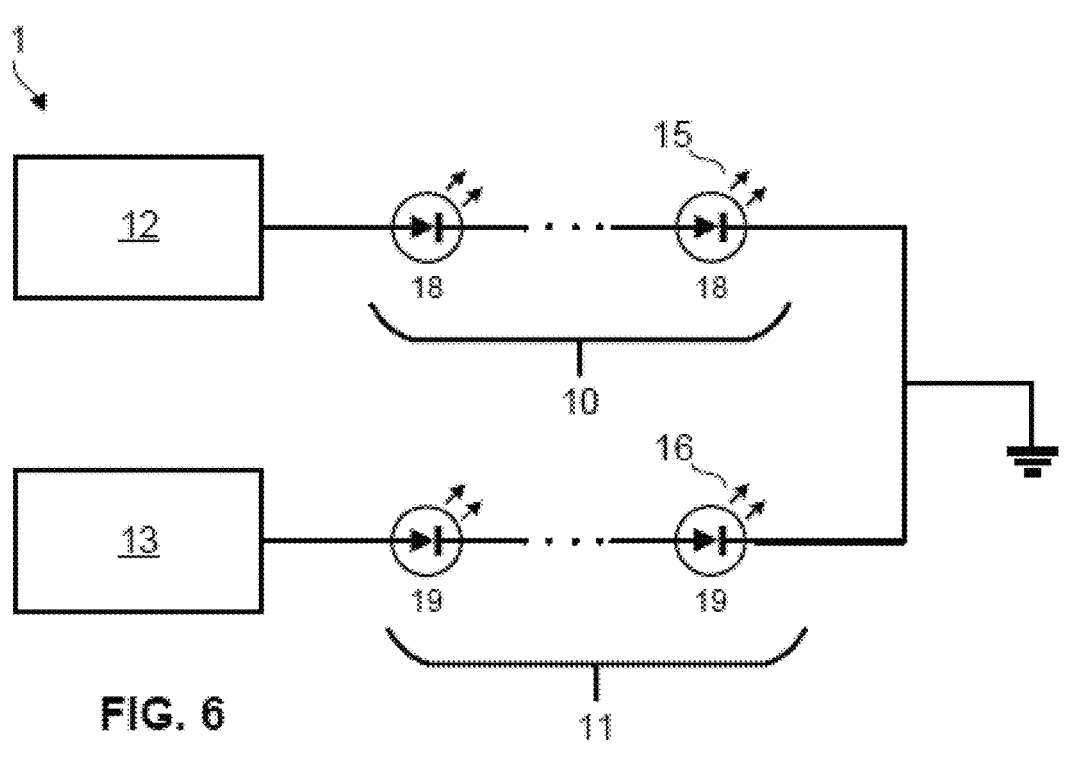
FIG. 6 is a schematic diagram of a lighting arrangement that may be used in some embodiments of the present disclosure.

FIG. 6 schematically presents a lighting arrangement 1 that may be used in the light tube 2b (or in any of the other suitable embodiments). The first light source 10 may comprise a plurality of LEDs 18, the number and light properties of which may be similar to what is described herein. The second light source 11 may comprise a plurality of LEDs 19 providing visible light, such that the combined light sources 10 and 11 provide white light suitable for general lighting. The driver circuit 12 may provide a pulsed driving current so that the first light source 10 emits pulsed red light with properties as described herein. Another driver circuit 13 may provide a driving current so that the light source 11 emits light such that the combined light from the first and second sources 10 and 11 provide white light suitable for general lighting without substantial perceptible flicker.

Figure 3:
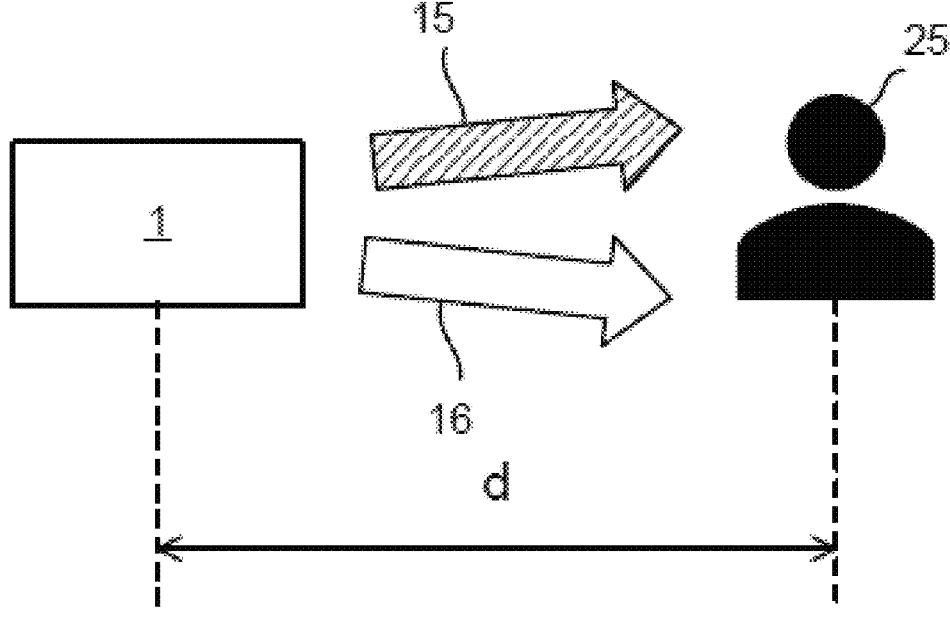
FIG. 3 illustrates a usage scenario of a lighting arrangement accordance with an embodiment of the present disclosure.

FIG. 3 illustrates a usage scenario of the lighting arrangement 1 in accordance with an embodiment of the present disclosure. In FIG. 3, the lighting arrangement 1 emits pulsed red light 15 and full-spectrum white light 16. A user 25 is a distance d away from the lighting arrangement 1. The distance d may be, for example, 1 meter. The full-spectrum white light 16 illuminates the surroundings of the user 25. The user 25 is also exposed to the pulsed red light 15. The power density enabled by (or resulting from) the red light 15 that the user 25 is exposed to depends on factors such as the distance d and the radiation pattern.

As a non-limiting example, assume that the first light source 10 has an optical emission power of 500 W with a peak wavelength of 660 nm light in order to enable a power density of 8 $mW/cm^2$ at a 2 m distance from the first light source 10. If the first light source 10 is operated in CW mode (i.e., constant optical emission of 500 W), then the required amount of electrical power is 1000 W assuming an electric-to-optical-power-conversion efficiency of 50%. In this example, the user 25 at a 2 m distance from the lighting arrangement 1 could be exposed to a power density of 8 mW/cm$^2$, sufficient to induce PBM response. The dosage (energy density) that the user 25 receives is 8 mW/cm$^2$ multiplied by the exposure time.

The first light source 10 in the above non-limiting example may be operated or driven in a different manner that provides additional benefits, as explained below.

Figure 4:
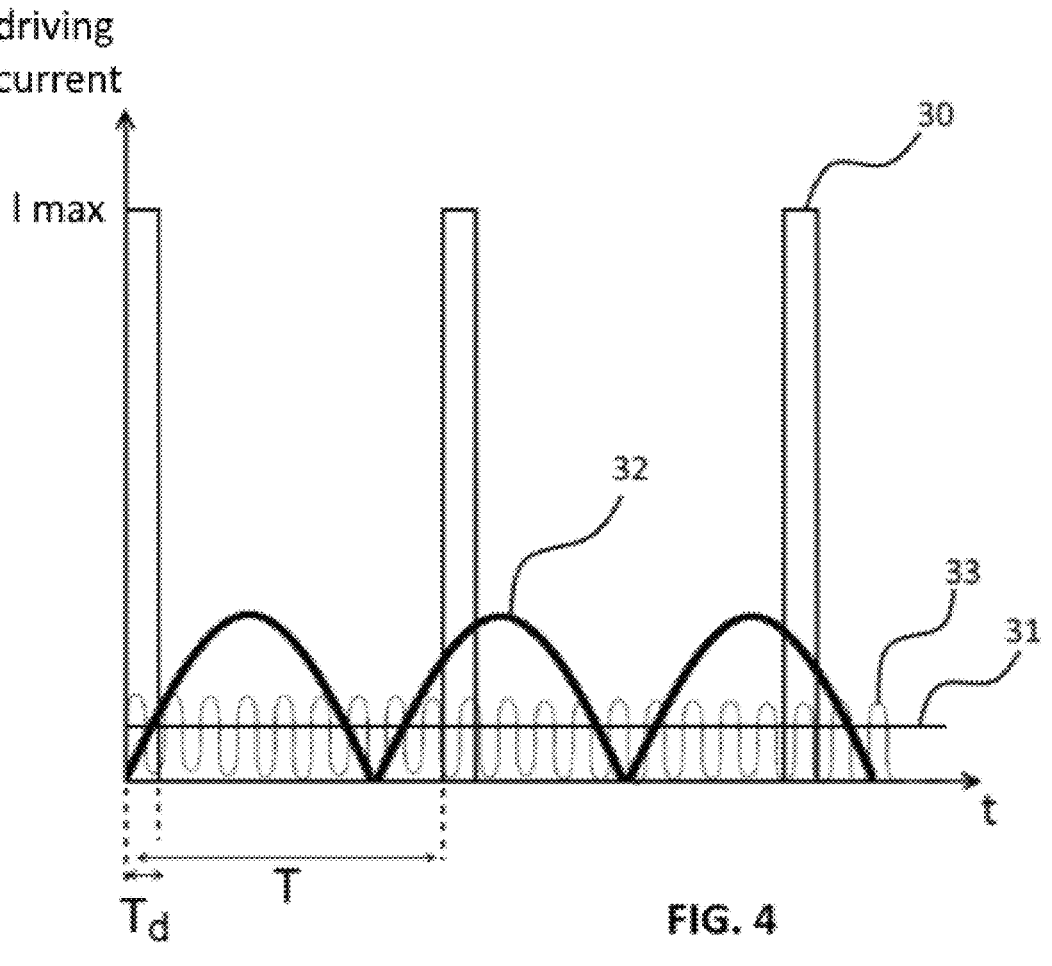
FIG. 4 is a graph of driving currents over time in a lighting arrangement in accordance with an embodiment of the present disclosure.

FIG. 4 illustrates a graph of various driving currents over time period tin a lighting arrangement 1 in accordance with an embodiment of the present disclosure. Curve 30 represents the first driving current 20, and curves 31, 32 and 33 represent various possibilities for the second driving current 21. As illustrated, the first driving current 20 represented as curve 30 is pulsed, having a pulse duration T$_d$, a pulse period T, and pulse amplitude I$_{max}$.

The second driving current 21 is adapted to drive the second light source 11 to provide full-spectrum white light having a steady substantially flicker-free light intensity suitable for general lighting purposes. The second driving current 21 may take various forms, such as a steady DC current (curve 31), a rectified AC current (curve 32), or a high-frequency pulsed current (curve 33). For example, the rectified AC current (curve 32) may have a frequency of, e.g. 100 or 120 Hz, suitable for driving light sources such as a low voltage halogen lamp. As another example, the pulsed current (curve 33) may be a pulse-width modulated (PWM) driving current having a pulse frequency in the range about 20-300 kHz, optionally 50-300 kHz. Pulsing the second light source 11 at these frequencies may provide dimming control without generating flicker perceptible by the human eye. It is evident that the scale in FIG. 4 is only for illustration only and is not exact.

According to this embodiment, the first light source 10 is driven by the first driving current 20 in a pulsed manner in order to produce short pulses of the red light 15 of relatively high light intensity, while the second light source 11 is driven by the second driving current 21 in order to produce light 16 having a steady substantially flicker-free light intensity suitable for general lighting purposes.

By generating the red light 15 in short pulses at high intensities, the high optical power density necessary to induce a PBM response can be achieved. To induce a PBM response in a human, a certain energy density of the red light 15, e.g. between 615-690 nm, is required. Literature suggests to target an optical power density range of 1-20 mW/cm$^2$ in the red light part of the spectrum on the surface of the human body, to achieve a substantial dose response causing a variety of beneficial systemic effects in the human body.

Conventional general lighting cannot achieve useful optical power density for PBM in common everyday use, unless the user is very close to the light source. For example, the effective optical power for PBM in a standard 100 W incandescent bulb over the full red and NIR spectrum is about 10 W (the full incandescent spectrum is about 10 times the spectrum useful for PBM), resulting in an effective power density of about 0.04 mW/cm$^2$ at a distance of 2 m from the light source, which at least one order of magnitude lower than the threshold intensity needed to stimulate significant biological effects.

Sufficient optical power density for PBM may be achieved by pulsing the light source. Although it would be possible to pulse a conventional light source to achieve a PBM effect, this would have the disadvantage of producing flicker perceptible to the human eye unless the pulses were very short pulses at very high frequency, e.g. pulse width of about 0.1 ms at a frequency of about 1 kHz, assuming a ten-fold intensity increase was needed compared with driving the light source in a steady-state CW or quasi-CW mode. Note that conventional light sources such as white LEDs or fluorescent tubes have a low amount of red light and NIR emissions, while incandescent bulbs have higher red light and NIR emissions but cannot be pulsed at such high frequencies.

The lighting arrangement 1 having a red light source 10 which is pulsed and a full-spectrum white light source 11 which is driven to emit steady-state light (e.g. not pulsed or pulsed at a sufficiently high frequency so that the flicker is essentially not perceptible) has the advantage that the flicker perception of the human eye is lower if only parts of the light spectrum are pulsed, especially if the pulsed light is in the red part of the light spectrum, and even more in the deep-red part of the spectrum between 640-690 nm. This lower flicker perception of pulsed red light is due to the circumstance that flicker perception is (at least partly) dependent on the generalized intensity perception over all wavelengths (dependent on the eye sensitivity at a wavelength, averaged over all wavelengths). Thus, in the lighting arrangement 1 which combines steady-state white light 16 with pulsed red light 15, the human eye notices only a small amount of flicker, since the eye factors in the non-pulsed, broadband white light in an additive way, resulting in a low average flicker perception. This phenomenon is called "chromaticity flicker".

The perception of light flicker in limited parts of the white light spectrum (chromaticity flicker) is especially decreased if the flickering part of the light is located at the edge of optical eye sensitivity. Deep-red light is located at the edge of the eye sensitivity curve, so that the flicker perception is further reduced since the eye sensitivity bottoms out. This makes it possible to use pulsed (deep) red light 15 which is 100% modulated at a relatively low frequency, but the human eye is not able to perceive the flicker when the pulsed red light 15 is combined with constant broadband white light 16. In addition, the more optical watts of red light contained in the steady-state white light 16, the less the flicker of the pulsed red light 15 is visible.

Referring back to FIG. 4, the first driving current 20 has a pulse duration of T$_d$ and a pulse period T. The duty cycle is T$_d$ divided by T. During the pulse, the first light source 10 is operated at maximum emission; in between the pulses, the first light source 10 is turned off.

As a non-limiting example, assume that the pulse duration of T$_d$ is 0.1 ms and the pulse period is 5 ms (i.e. a pulse frequency of 200 Hz), namely a duty cycle of 2%. If the first light source 10 delivers a power density of 8 mW/cm$^2$ at a 2 m distance during the pulse, sufficient to induce a PBM response, the average power of the first light source is only 2% of the power required if the first light source was not pulsed. Pulsing the first light source 10 can produce the PBM response-inducing level of power density at a much lower electrical power.

Another consequence of pulsing the first light source 10 is that the radiation dosage (related to energy density) received by the user over a certain time period decreases by the corresponding duty cycle. This lower dosage decreases the risk of over-dosage, enabling the user to remain exposed to the lighting arrangement 1 over long periods, much longer than a typical treatment period of 30 to 60 minutes at a specialist center. For example, some medical research suggests that the beneficial biological response peaks at a dosage of about 10 J/cm$^2$, and the PBM response may cease to be beneficial if the dosage exceeds about 35 J/cm$^2$. Thus, if a user is exposed to an optical power density level of about 8 mW/cm$^2$ for more than about 60 minutes, then it would be hard for the user to receive the peak benefit. In other words, sufficiently short pulse duration and/or period may provide sufficient power density to induce PBM responses and at the same time deliver an appropriate amount of total energy density (which is power per unit area multiplied by time) over, e.g., 6 hours or more, without overdosing the user. That way, the user may use the lighting apparatus as if it were a conventional light source without any need to worry about when to switch it off (to prevent overdosage) and yet can still receive the benefit of PBM-inducing radiation.

The addition of the pulsed red light 15 to the light 16 causes a colour shift of the perceived integral optical value of the combined light. If more pulsed red light 15 is added, the integral measured colour point may shift into the red, away from the black body curve. In an embodiment, the addition of the pulsed red light 15 from the first light source 10 does not significantly move the colour point of the combined light (15 and 16) from the black body line. In an embodiment, the light 16, which may lack significant light in the red spectrum, may be corrected by the red light 15 such that the combined light 15 and 16 has the colour point close to the black body line. The combined color point resulting from adding the pulsed red light 15 to the light 16 is preferably determined by an integral measurement, i.e. measuring the average colour point over a sufficiently long time period so that the average of the pulsed red light combined with the white light can be measured.

In an embodiment, the combination of the red light 15 from the first light source 10 and the light 16 from the second light source 11 has an average color point in the CIE x,y chromaticity space that has a distance less than 8 SDCM to a black body line in the color space.

The amount of optical power that may be added by the pulsed red light 15 while achieving this depends on the colour temperature of the light 16. The table below shows the amount of pulsed red light 15 that may be present, expressed as a percentage of the total optical power of the combined light (from both the first and second light sources 10, 11) for a desired colour temperature of the combined light. The right-hand column shows the maximum red light present in the combined light:

| Desired colour temp. | Maximum |
|---|---|
| 2700 K | 40% |
| 3000 K | 35% |
| 4000 K | 20% |
| 5000 K | 6% |

At lower colour temperatures such as 2700K, regulating the amount of added pulsed red light 15 may be used to red-dim the spectrum towards lower colour temperatures such as 2500K or lower, since the integral colour point will shift mainly in parallel to the black body curve into the red region when the integral value of the optical power of the red light is increased.

Figure 5:
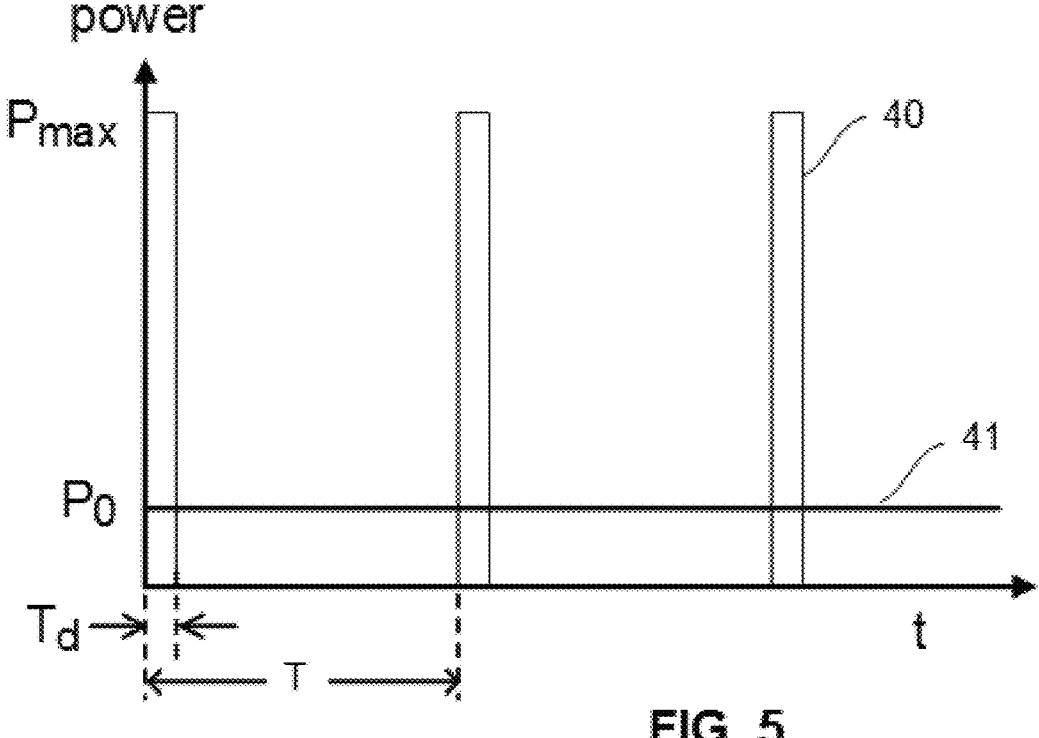
FIG. 5 is a graph of emission power over time from lighting arrangement in accordance with an embodiment of the present disclosure.

FIG. 5 illustrates a graph of optical power over time of the first light source 10 and the second light source 11 of a lighting arrangement in accordance with an embodiment of the present disclosure. Curve 40 represents the pulsed red light 15, and curve 41 represents the full-spectrum white light 16. If the first light source 10 and the light source 11 can react essentially instantly to the respective driving signals 20, 21, then the shape of the pulsed red light 15 and visible light 16 will match the respective driving signals; if not, delays and transients may occur. For example, the intensity of light emitted by a thermal emitter such as an incandescent bulb driven by a rectified AC current would change more slowly than the driving rectified AC current because of thermal inertia. As another example, driving an LED with a PWM signal at a sufficiently high frequency range suitable for dimming control may create light that looks substantially constant to the human eye. The inventive concept behind the embodiments, however, would stay substantially identical.

The following examples show how to apply the inventive concepts behind the above-discussed embodiments in some types of lighting apparatuses. The examples are for illustration only, non-exhaustive and not limiting.

Two-Phosphor System with Pulsed Deep-Red LED(s)

LED phosphor systems which create white light using an LED emitting blue light as a primary emitter (referred to as a "pump") combined with two or more phosphors are very common in today's lighting market. The phosphors may be applied onto the blue pump LED to cover its light emitting surface, or arranged remotely from the blue pump LED so that light from the LED enters the phosphors.

Typically used phosphors, which convert parts of the blue light originating from the blue LED source, are the YAG:Ce phosphor with dominant wavelength in the green part of the light spectrum (e.g. YAG2.7 with a peak emission at around 560 nm) in combination with a CASN phosphor with dominant wavelength in the red part of the light spectrum (e.g. CASN615 with a peak emission at around 615 nm). The light spectrum of LEDs combining a blue LED with green and red phosphors typically has a colour rendering index (CRI) between 75 and 85, which is suitable for most applications in general lighting. Without the red phosphor the CRI value would not exceed 70, which is considered too low for general lighting applications.

In some embodiments, the red phosphor(s) of a white LED can be wholly or partly replaced by a pulsed LED emitting light in the deep-red part of the light spectrum, to provide or contribute to the red part of the visible spectrum to obtain a suitable CRI value while also providing photo-biological stimulation. Such deep-red light emitting LEDs are commonly available on the market from various LED suppliers, usually referred to as "deep-red" or "photo-red" LEDs.

The benefit of replacing some amount of or all the light originally emitted by a red phosphor by light emitted from one or more pulsed LEDs emitting deep-red light, is that a similar optical stimulation can be achieved in combination with the health benefits of photobiomodulation (PBM). Additionally, the number of phosphors could be reduced, e.g only one phosphor may be required if all (or substantially all) of the red part of the spectrum was supplied by the pulsed LEDs instead of a red phosphor, which could lead to manufacturing and costs advantages. To achieve a significant PBM effect, the deep-red LED is pulsed at a specific frequency and pulse width, with an optical power sufficient to generate sufficient biological stimulation in human cells.

In some embodiments, this is achieved without changing the achieved resulting colour point of the light spectrum (e.g. in the CIE 1976 diagram).

Figure 7:
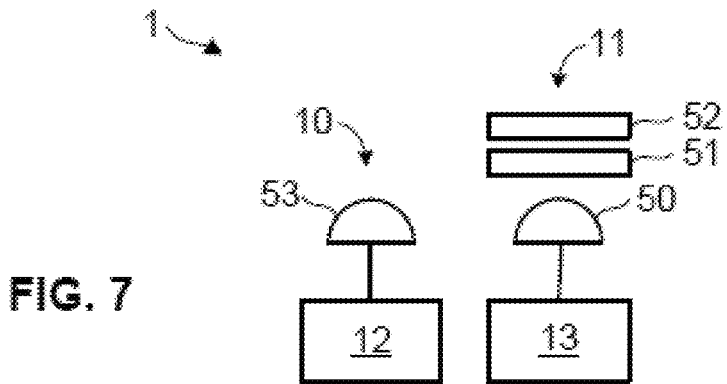
FIG. 7 is a schematic diagram of an embodiment of a lighting arrangement including a two-phosphor system.

FIG. 7 is a schematic diagram of one embodiment of a lighting arrangement 1 similar to the embodiment of FIG. 1B, wherein the second light source 11 comprises a one or two-phosphor system which includes a pump LED 50 emitting light substantially in the violet or blue or purple part of the light spectrum, e.g. in the range 380 nm to 490 nm, in combination with one or two phosphors 51, 52 (shown schematically). The system may comprise a green phosphor 51 and an optional red phosphor 52. The first light source 10 comprises a pulsed deep-red LED 53 as in the previous embodiments. The lighting arrangement 1 may e.g. produce combined light from the first and second light sources 10, 11 with a colour temperature of 2700K.

Example Embodiment 1

Two-phosphor System with Pulsed Deep-Red LED(s)

In example embodiment 1 of the two-phosphor embodiment of FIG. 7, the pump LED 50 has a peak emission at around 450 nm, the green phosphor 51 comprises a YAG 2.7 phosphor, the red phosphor 52 comprises a CASN615 phosphor, and the pulsed deep-red LED has a peak emission at around 650 nm. The approximate optical fractions of these components are shown in Table 1 below for this example embodiment, compared with the optical fractions of a typical conventional two-phosphor system comprising the same components 50-52 (except the pulsed deep-red LED 53).

TABLE 1

|  | Pump LED 50 | Green phosphor 51 | Red phosphor 52 | Pulsed deep-red LED 53 |
|---|---|---|---|---|
| Example values | peak at 450 nm | YAG 2.7 | CASN615 | peak at 650 nm |
| Example embodiment 1 | 7% | 49% | 25% | 19% |
| Conventional two-phosphor system | 8% | 42% | 50% | — |

In example embodiment 1, the optical power of the red phosphor 52 is reduced in comparison to the conventional system, to allow adding optical watts by the pulsed deep-red LED, while keeping a similar colour point and correlated colour temperature (CCT) compared with the conventional system.

Figure 8A:
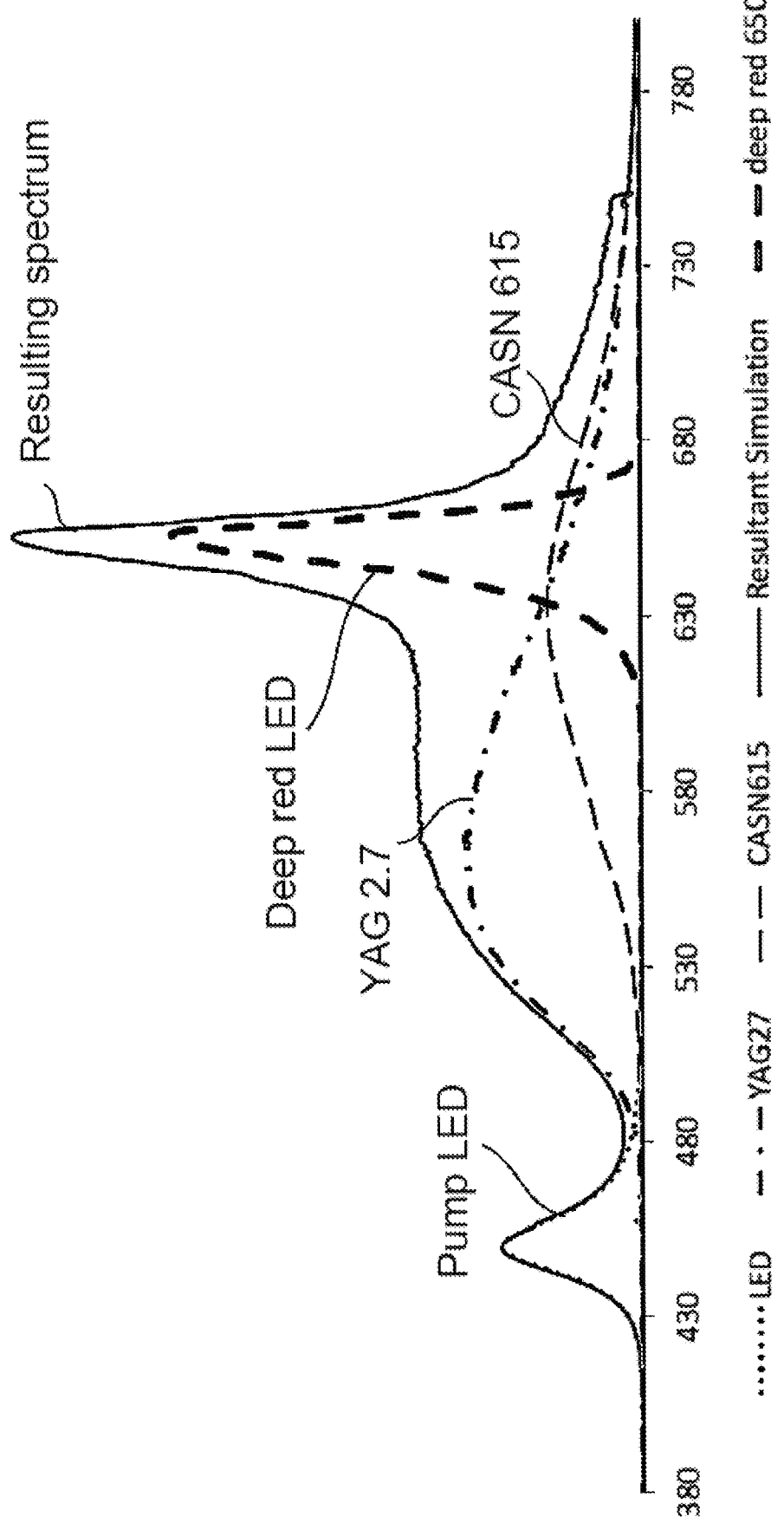
FIG. 8A is a diagram of a light spectrum of a lighting arrangement in accordance with the embodiment of FIG. 7.
Figure 8B:
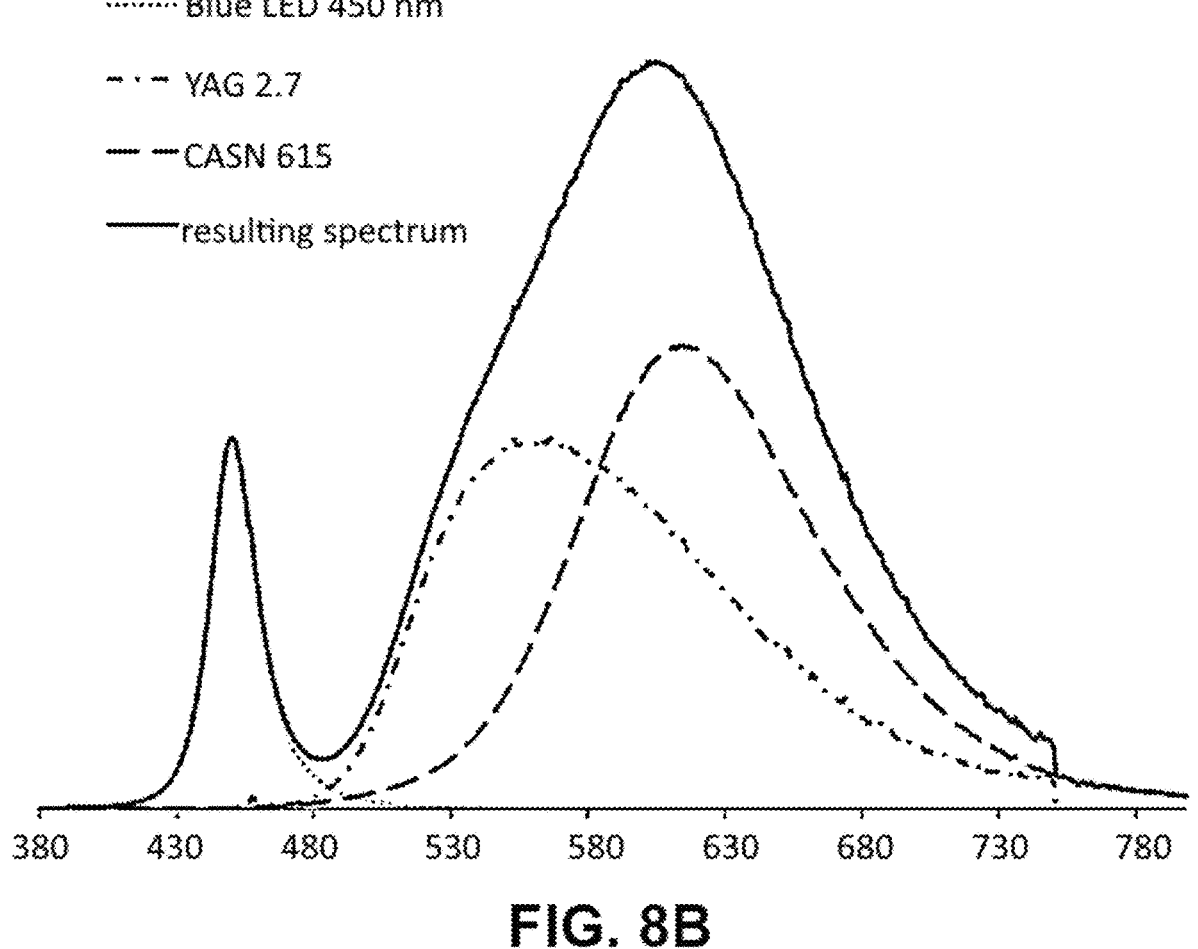
FIG. 8B is a diagram of a light spectrum of a conventional lighting arrangement including a two-phosphor system.

A diagram of the light spectrum for example embodiment 1 and for the conventional two-phosphor system described above are shown in FIGS. 8A and 8B respectively. The x-axis is wavelength of the emitted light and the y-axis indicates the relative magnitude of the contributions of each component as a function of wavelength which combine to produce the total resulting light spectrum.

Figure 9A:
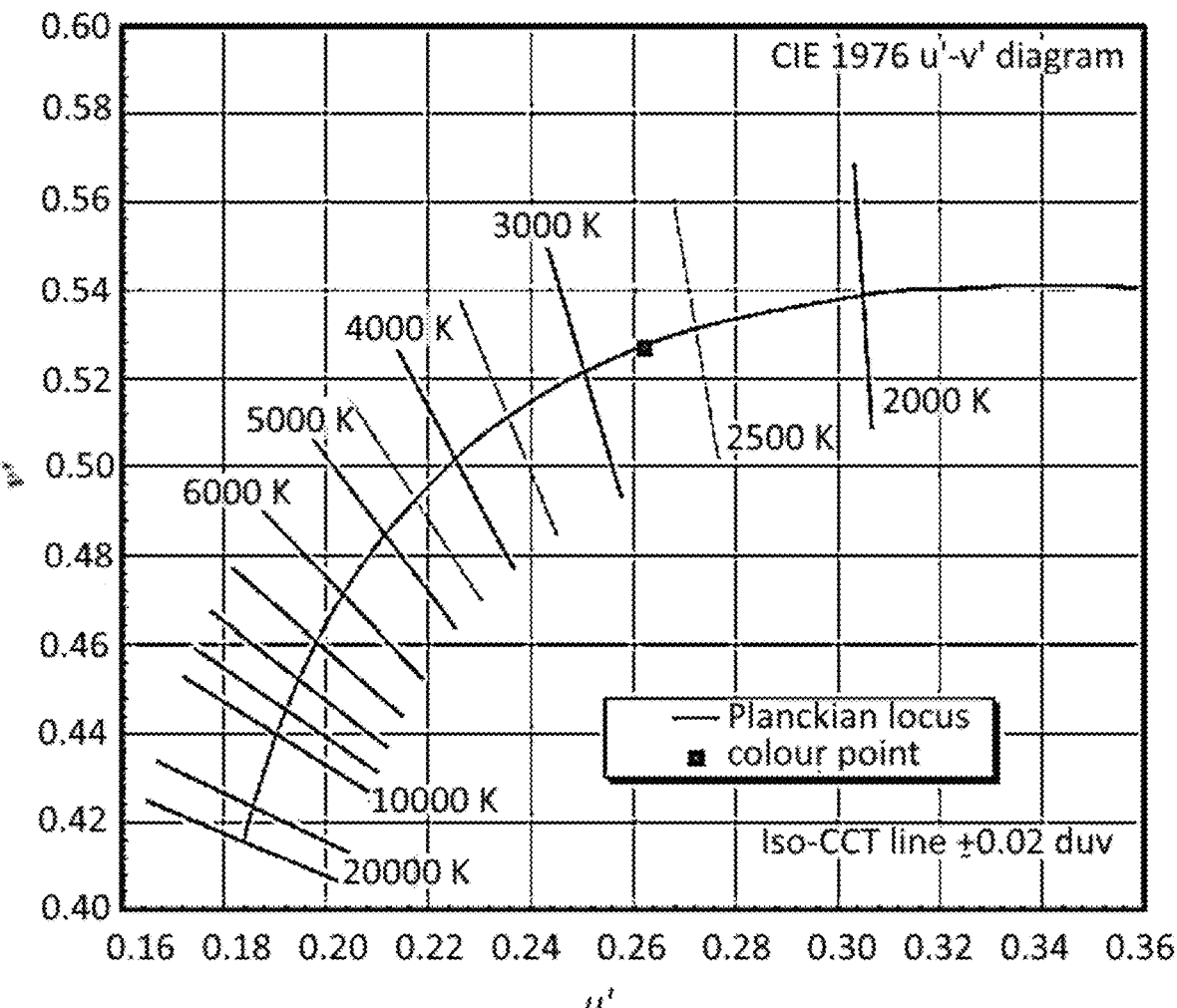
FIG. 9A is a CIE 1976 diagram showing the colour point for a lighting arrangement in accordance with the embodiment of FIG. 7.
Figure 9B:
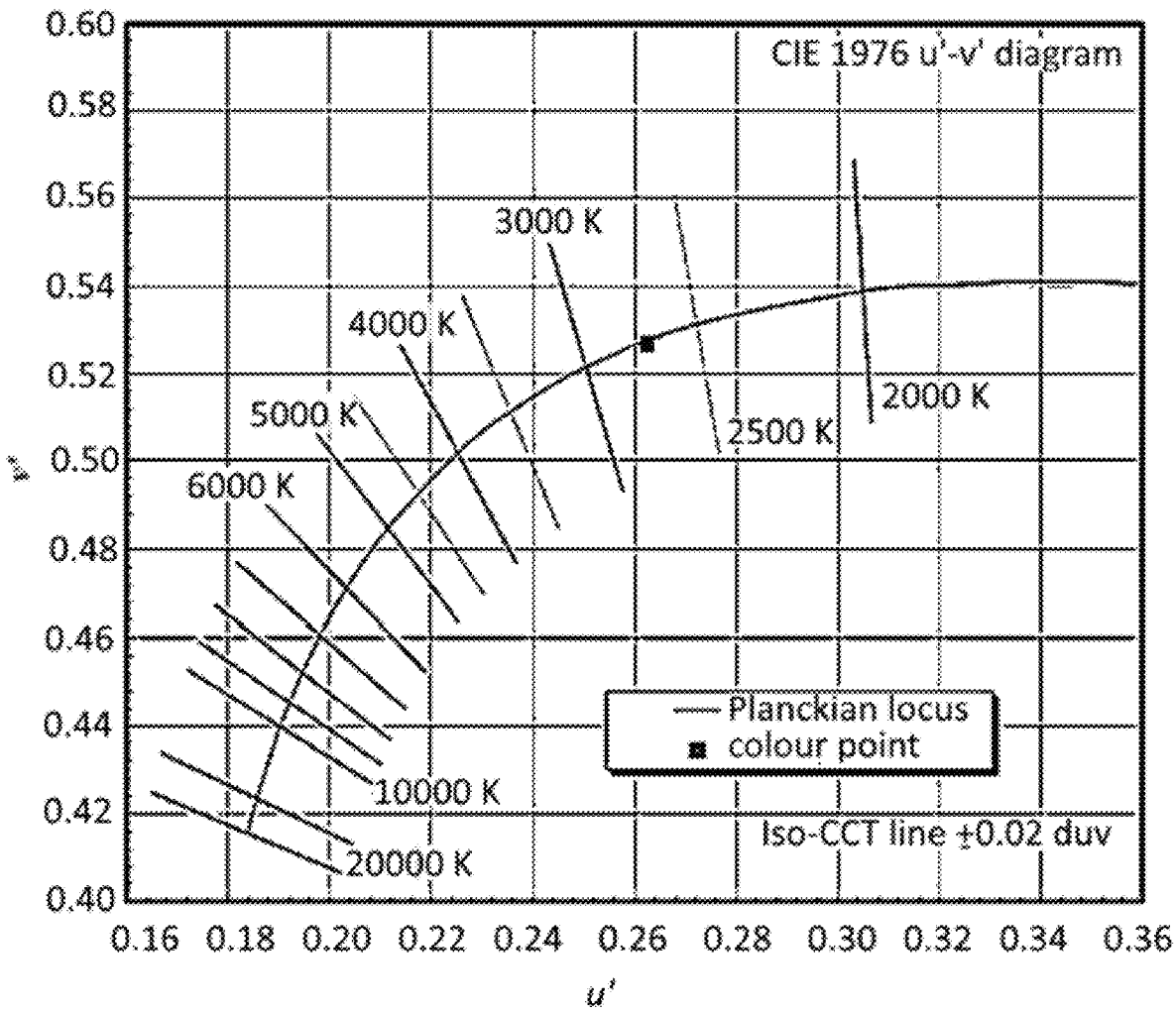
FIG. 9B is a CIE 1976 diagram showing the colour point for a conventional lighting arrangement including a two-phosphor system.

The resulting colour point in the CIE 1976 diagram for example embodiment 1 and for the conventional system are shown in FIGS. 9A and 9B respectively. As can be seen, the colour point of the two systems is almost identical.

The correlated colour temperature (CCT) and colour rendering values of example embodiment 1 are shown in the two left-hand columns of Table 2 below, and for the conventional system are shown in the two right-hand columns of Table 2:

TABLE 2

| CCT | 2713 | CCT | 2704 |
|---|---|---|---|
| R1 | 90.8 | R1 | 78.1 |
| R2 | 88.7 | R2 | 85.0 |
| R3 | 79.7 | R3 | 88.7 |
| R4 | 89.3 | R4 | 76.4 |
| R5 | 87.2 | R5 | 74.8 |
| R6 | 78.3 | R6 | 76.2 |
| R7 | 90.2 | R7 | 87.0 |
| R8 | 93.5 | R8 | 67.6 |
| R9 | 97.5 | R9 | 25.8 |

TABLE 2-continued

| CCT | 2713 | CCT | 2704 |
|---|---|---|---|
| R10 | 69.9 | R10 | 62.8 |
| R11 | 85.3 | R11 | 69.7 |
| R12 | 56.2 | R12 | 49.1 |
| R13 | 89.2 | R13 | 78.7 |
| R14 | 87.2 | R14 | 92.7 |
| Ra | 87.2 | Ra | 79.2 |

As can be seen in Table 2, the CCT values are very similar for the two systems, indicating that the light from the two systems will be difficult to be distinguish visually from each other. However, the spectrum of the lighting arrangement with pulsed deep red LED has a significantly better colour rendering, especially on the R9 value, compared with the conventional system, so that the optical perception of colours is much improved compared to the conventional system.

In example embodiment 1 described above, the first light source 10 (the pulsed deep-red LED 53) contributes a relative optical fraction of approximately 19% of the total, average optical power from the lighting arrangement. To reduce visible flicker from the first light source 10 to an acceptable level (e.g. no significant visible flicker), the pulse frequency and pulse width of the driving current 20 of the first light source 10 should be set at values which deliver the required optical power to induce a PBM effect with sufficiently short pulses to avoid significant visible flicker.

For example embodiment 1, examples of suitable arrangements for driving the first light source 10 are shown in Table 3 below. For each driving arrangement, the pulsed driving current 20 of the first light source 10 is provided at the indicated pulse frequency, duty cycle and pulse width, and is adapted to deliver the indicated approximate peak power density during a pulse of the current at a distance to the light emitting window of the lighting arrangement where a total of 500 lux is measured.

TABLE 3

|  | Frequency | Duty cycle | Pulse width | Approx. Peak power density | Accumulative dose over 8 hours exposure | SVM |
|---|---|---|---|---|---|---|
| Example A | 100 Hz | 3.1% | 0.31 ms | 1 mW/cm$^2$ | 0.9 J/cm$^2$ | 0.6 |
| Example B | 200 Hz | 3.1% | 0.16 ms | 1 mW/cm$^2$ | 0.9 J/cm$^2$ | 0.42 |

Note that example B shown above is less preferred, as the pulse width is very short and may be insufficient to induce significant PBM effects. However, further increasing the frequency does improve the SVM results.

An increase in pulse width, and increase in optical intensity, of the first light source 10 is limited to avoid significant visible flicker. Furthermore, an increase in pulse width will increase the relative optical fraction of the red light in comparison to the total spectrum, moving the colour point of the combined light from the lighting arrangement.

The above described procedure can also be applied in a similar fashion on other phosphor systems using red phosphors, for example phosphor systems in LEDs using red CASiN phosphors with another dominant wavelength, for example "CASN 645", which has a dominant wavelength further in the red part of the light spectrum at 645 nm. The above described driving arrangements can also be applied in a similar fashion on other phosphor systems.

Multi-Phosphor System with Pulsed Deep-Red LED(s)

Some LED light sources on the market use multiple phosphors to try to produce a light spectrum similar to natural sunlight in the visible region. Examples of LEDs containing such spectral compositions are the "SunLike" LED products from Seoul Semiconductor and the "Optisocomponents are shown in Table 4 below for this embodiment, compared with the optical fractions of the Optisolis five-phosphor system comprising the same components 60-64, with the addition of an MGF phosphor 65 (and not including the pulsed deep-red LED 66).

TABLE 4

| | Pump LED 60 | Phosphor 61 | Phosphor 62 | Phosphor 63 | Phosphor 64 | Phosphor 65 | Pulsed LED 66 |
|---|---|---|---|---|---|---|---|
| Example values | 420 nm | BAM | Silicate Eu2+ | LuAG | CASN615 | MGF | 650 nm |
| Example embodiment 2 | 1.62% | 3.28% | 5.87% | 18.68% | 62.78% | — | 7.77% |
| Convention. 5-phosphor system | 1.68% | 3.34% | 5.50% | 17.36% | 60.40% | 11.72% | — | lis" LED products from Nichia Corporation which produce a light spectrum that achieves a close match to that of both the sun and incandescent lights in the visible light spectrum.

The light spectrum of such products typically have a high CRI value of close to 100, which means the colour of objects illuminated with this light spectrum appear to the human eye in a natural way comparable to how they would be visually perceived in natural sunlight during the day (e.g. at 5000K colour temperature) or also compared to incandescent light or sunlight in the evening (e.g. at 2700K colour temperature).

Besides the improved optical stimulation of the eye enabling to perceive the colour of illuminated objects in a natural way, there is a further human psychological benefit due to the naturally occurring colours, which is thought to improve the well-being of people who are exposed to this light spectrum for a significant period.

The complex spectral composition of LEDs emitting this type of "natural" light spectrum are commonly created using a violet pump LED in combination with a variety of different phosphors. For example, the "Optisolis" LEDs uses a pump LED with a dominant wavelength of 420 nm in combination with five different phosphors.

Figure 10:
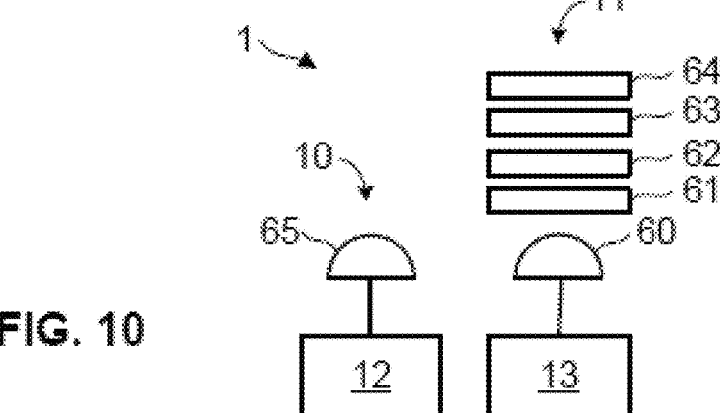
FIG. 10 is a schematic diagram of an embodiment of a lighting arrangement including a four-phosphor system.

FIG. 10 is a block diagram of one embodiment of a lighting arrangement 1 similar to the embodiment of FIG. 1B, where the lighting arrangement is designed to produce light closely matching natural sunlight. In this embodiment, the second light source 11 comprises a four-phosphor system which includes a pump LED 60 emitting light substantially in the violet part of the light spectrum, e.g. in the range 380 nm to 450 nm, in combination with four phosphors 61-64 (shown schematically). The first light source 10 comprises a pulsed deep-red LED 66 as in the previous embodiments. The lighting arrangement 1 may e.g. produce combined light from the first and second light sources 10, 11 with a colour temperature of 2700K.

Example Embodiment 2

Multi-Phosphor System with Pulsed Deep-Red LED(s)

In example embodiment 2, the pump LED 60 has a peak emission at around 420 nm, and the four phosphors comprise e.g. a BAM phosphor 61, a Silicate Eu2+ phosphor 62, an LuAG phosphor 63, and a CASN615 phosphor 64, combined with a pulsed deep-red LED 66 with a peak emission at around 650 nm. The approximate optical fractions of these In the conventional Optisolis five-phosphor system, the MGF phosphor 65 has its dominant wavelength in the deep red part of the light spectrum around 650 nm. In example embodiment 2 this phosphor is replaced by the pulsed deep-red LED 66, to provide both the red light component required to achieve the desired light closely matching natural sunlight, and to additionally provide photobiological stimulation.

In example embodiment 2, the relative optical fraction (of the total in %) of the pulsed deep-red LED 66 is reduced in comparison to the relative optical fraction of the MGF phosphor 65 in the conventional system, achieving similar optical properties of the resulting total spectrum (e.g. colour temperature and Ra). As a result, the relative optical fraction of the remaining light emitters which contribute to the total spectrum have their relative optical fraction have slightly increased.

Figure 11A:
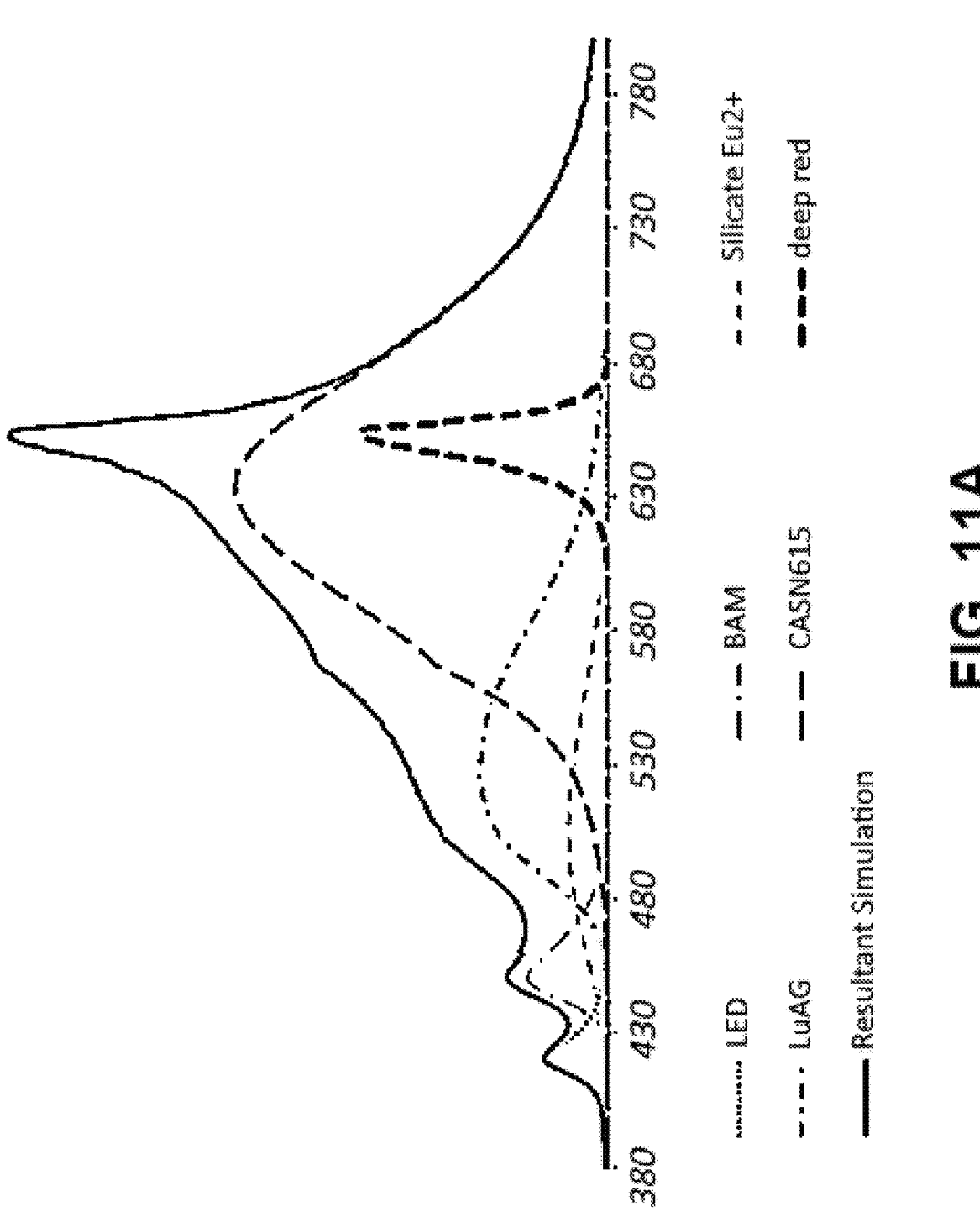
FIG. 11A is a diagram of a light spectrum of a lighting arrangement in accordance with the embodiment of FIG. 10.
Figure 11B:
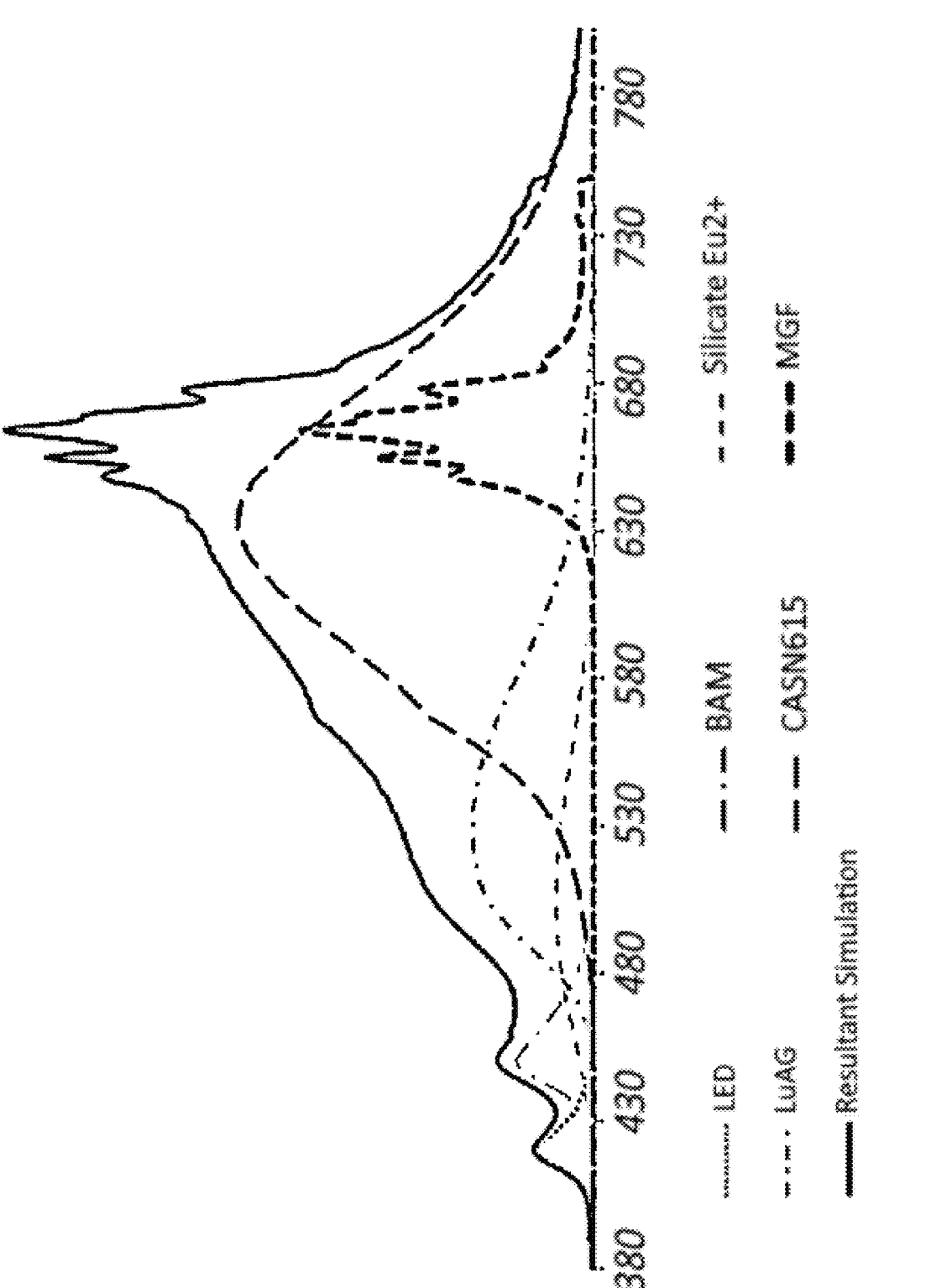
FIG. 11B is a diagram of a light spectrum of a conventional lighting arrangement including a four-phosphor system.

A diagram of the light spectrum for example embodiment 2 and for the conventional five-phosphor system described above is shown in FIGS. 11A and 11B respectively. The x-axis is wavelength of the emitted light and the y-axis indicates the relative magnitude of the contributions of each component as a function of wavelength which combine to produce the total resulting light spectrum.

Figure 12A:
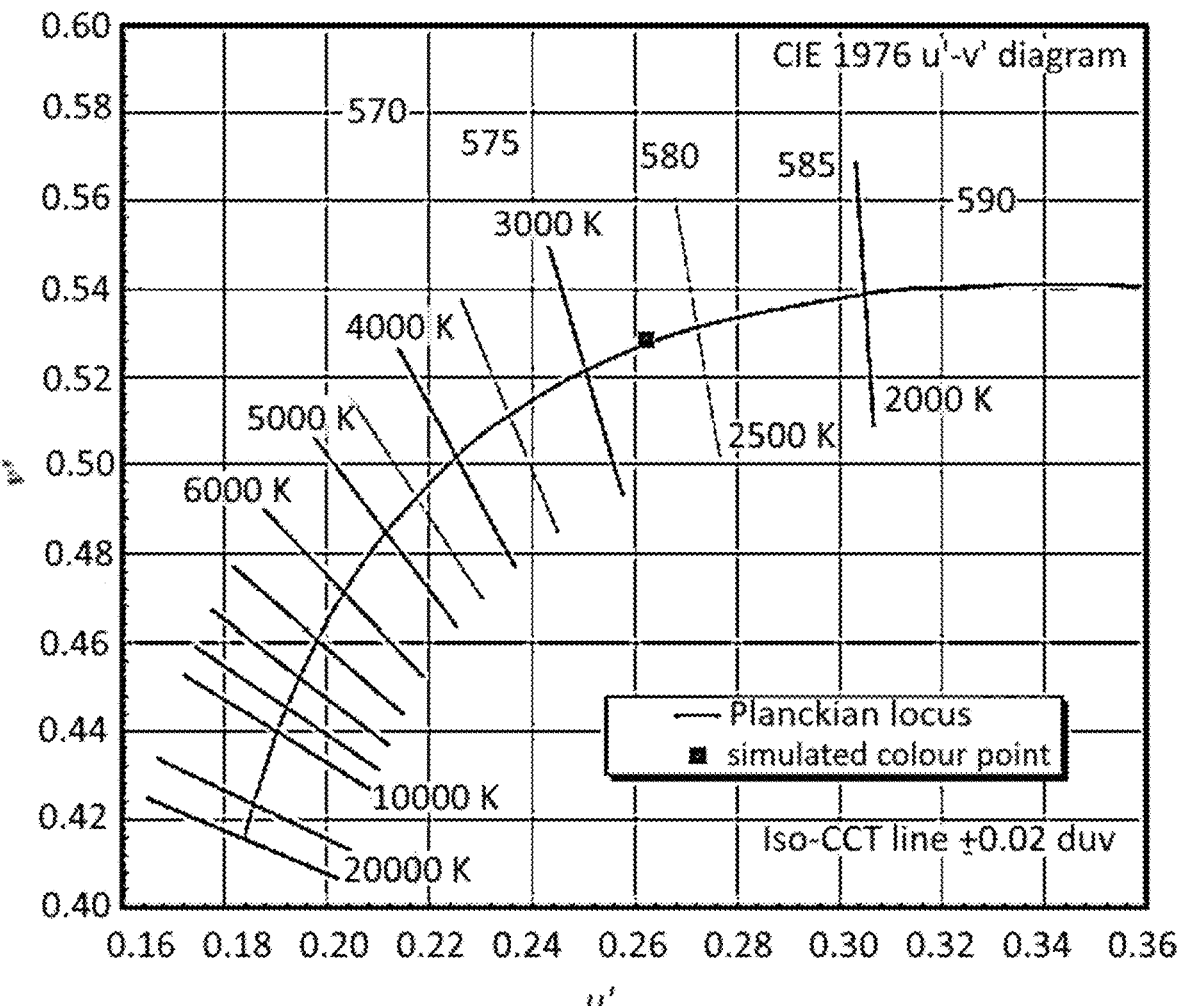
FIG. 12A is a CIE 1976 diagram showing the colour point for a lighting arrangement in accordance with the embodiment of FIG. 10.
Figure 12B:
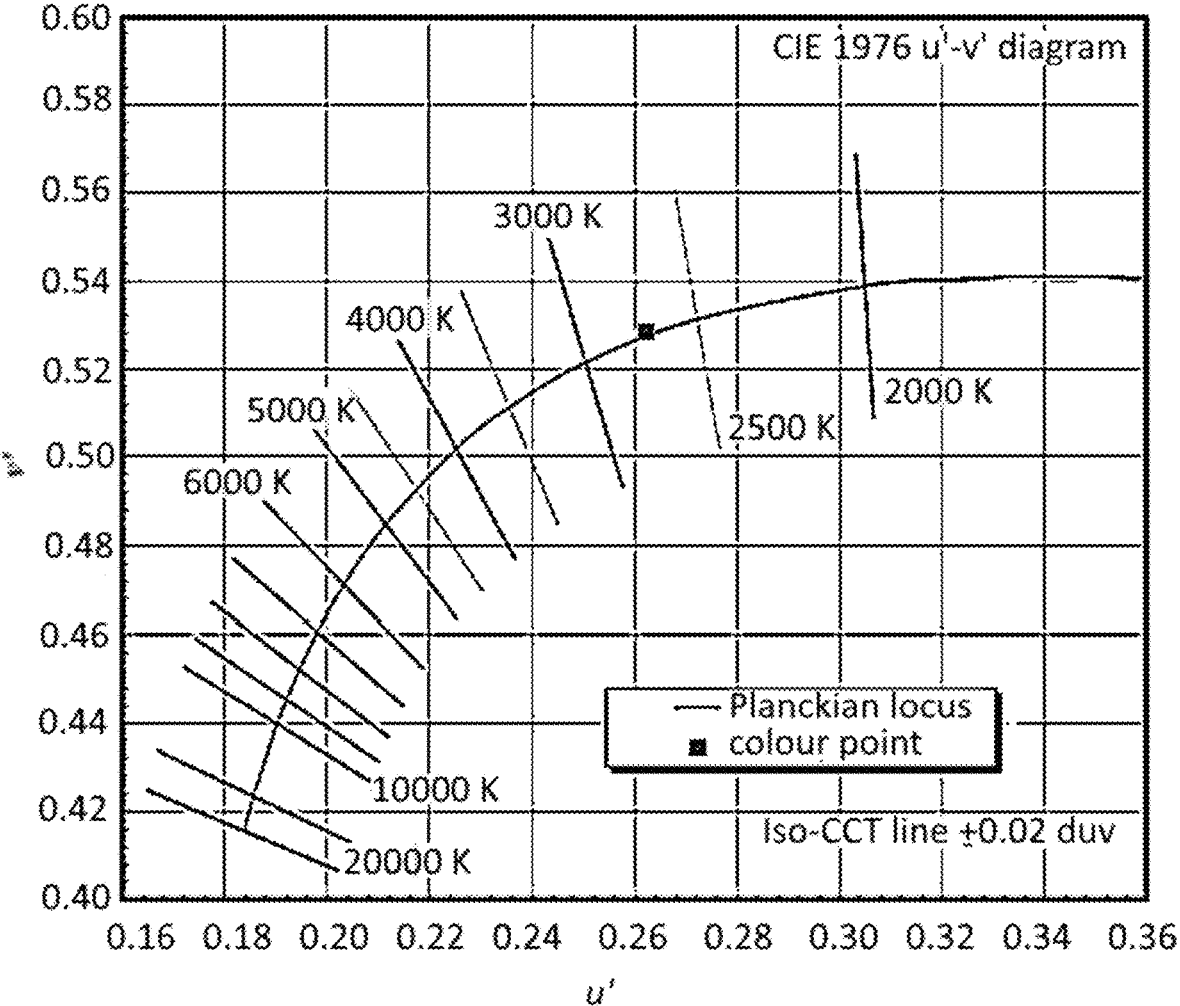
FIG. 12B is a CIE 1976 diagram showing the colour point for a conventional lighting arrangement including a four-phosphor system.

The resulting colour point in the CIE 1976 diagram for example embodiment 2 and for the conventional five-phosphor system is shown in FIGS. 12A and 12B respectively. As can be seen, the colour point of the two systems is almost identical.

The correlated colour temperature (CCT) and colour rendering values of example embodiment 2 are shown in the two left-hand columns of Table 5 below, and for the conventional five-phosphor system are shown in the two right-hand columns of Table 5:

TABLE 5

| CCT | 2700 | CCT | 2712 |
|---|---|---|---|
| R1 | 99.7 | R1 | 98.8 |
| R2 | 99.3 | R2 | 99.0 |
| R3 | 97.5 | R3 | 98.4 |
| R4 | 98.6 | R4 | 99.4 |
| R5 | 99.6 | R5 | 99.3 |
| R6 | 99.6 | R6 | 99.4 |
| R7 | 99.9 | R7 | 99.3 |
| R8 | 99.8 | R8 | 98.4 |
| R9 | 98.8 | R9 | 96.3 |
| R10 | 98.7 | R10 | 98.4 |
| R11 | 96.0 | R11 | 97.7 |
| R12 | 98.9 | R12 | 99.0 |

TABLE 5-continued

| CCT | 2700 | CCT | 2712 |
|---|---|---|---|
| R13 | 99.5 | R13 | 98.8 |
| R14 | 97.9 | R14 | 98.6 |
| Ra | 99.2 | Ra | 99.0 |

As can be seen in Table 5, the CCT and colour rendering values are very similar for the two systems, indicating that the light from the two systems will be difficult to distinguish visually from each other, e.g. the colours of objects illuminated by the two systems will appear to have similar colours.

In example embodiment 2, the first light source 10 (the pulsed deep-red LED 66) can contribute a relative optical fraction of approximately 6.59% of the total light emitted from the lighting arrangement 1 while avoiding significant visible flicker. As in the previously described embodiments, the pulse frequency and pulse width of the driving current 20 of the first light source 10 should be set at values which deliver the required optical power to induce a PBM effect with sufficiently short pulses to avoid significant visible flicker.

For example embodiment 2, examples of suitable arrangements for driving the first light source 10 are shown in Table 6 below. For each driving arrangement, the pulsed driving current 20 of the first light source 10 is provided at the indicated pulse frequency, duty cycle and pulse width, and is adapted to deliver the indicated approximate peak power density during a pulse of the current at a distance to the light emitting window of the lighting arrangement where a total of 500 lux is measured.

TABLE 6

| | Frequency | Duty cycle | Pulse width | Approx. peak power density | Accumu- lative dose over 8 hours exposure | SVM |
|---|---|---|---|---|---|---|
| Example A | 100 Hz | 1.5% | 0.146 ms | 1.00 mW/cm$^2$ | 0.42 J/cm$^2$ | 0.22 |
| Example B | 200 Hz | 1.5% | 0.073 ms | 1.00 mW/cm$^2$ | 0.42 J/cm$^2$ | 0.15 |

Note that example B shown above is less preferred, as the pulse width is very short and may be insufficient to induce significant PBM effects. An increase in pulse width, and increase in optical intensity, of the first light source 10 is limited to avoid significant visible flicker. Furthermore, an increase in pulse width will increase the relative optical fraction of the red light in comparison to the total spectrum, moving the colour point of the combined light from the lighting arrangement. However, further increasing the frequency does improve the SVM results.

One way to increase the amount of optical watts of the pulsed deep-red light without changing the total resulting light spectrum too far away from the black body curve (Planckian locus) is by adjusting the other components of the lighting arrangement 1 of FIG. 10. For example, by further reducing the relative optical fraction of the phosphor(s) emitting in the red part of the spectrum, e.g. the CASN615 phosphor 64 with dominant wavelength at 615 nm in example embodiment 2. In this way, a total optical fraction contributed by the pulsed deep-red LED 66 of more than 10% may be achieved. However, the resulting total spectrum will have slightly less optimal optical values regarding the achieved colour rendering values.

The above described driving arrangements can also be applied in a similar fashion on other phosphor systems.

Pulsed Deep-Red LED(s) and a Red Colour Shift

In the embodiment shown in FIG. 7, a two-phosphor system 51, 52 is combined with a pulsed deep-red LED 53. As noted previously, adding light in the deep-red part of the light spectrum (from the pulsed deep-red LED 53) will change the resulting colour point (e.g. in the CIE 1976 diagram) of the total light emitted by the lighting arrangement, possibly shifting the colour point into or towards the red part of the spectrum. The amount of optical watts added by the pulsed deep-red LED 53 is usually limited to less than about 10% of the total optical watts, unless the contribution of the red phosphor 52 (e.g. CASiN) is reduced, in comparison to a conventional two-phosphor system, to avoid shifting the colour point too far into the red resulting in lower colour rendering values.

However, in some embodiments wherein the lighting arrangement 1 produces light with a colour temperature at or below 3000K, especially at or below 2700K, higher amounts of optical watts can be produced by the pulsed deep-red LED 53 while accepting a colour shift of the resulting total spectrum into the red. This red shift of such low colour temperatures is acceptable, since the colour point in the CIE diagram shifts mainly parallel to the black body curve. This red shift at lower colour temperatures results in only a very small shift away from the black body curve, unlike the larger divergence observed at higher colour temperatures above 3000K, due to the orientation of the black body curve in the CIE u,v diagram.

The resulting red-shifted spectrum will still appear natural due to the close location of the colour point relative to the black body curve. This red shift is referred to as "colour temperature dimming".

Example Embodiments 3 and 4

Pulsed Deep-Red LED(s) and Red Colour Shift

In example embodiment 3, the lighting arrangement 1 emits warm white light (e.g. with an initial colour temperature of approximately 2700K) and the pulsed deep-red LED 53 provides approximately 20% of the total optical watts. In example embodiment 4, the pulsed deep-red LED 53 provides approximately 35% of the total optical watts. The approximate optical fractions of the components of a conventional two-phosphor system compared with example embodiments 3 and 4 are shown in Table 7.

TABLE 7

| | Pump LED 70 | Green phosphor 71 | Red phosphor 72 | Pulsed deep-red LED 73 |
|---|---|---|---|---|
| Example values | peak at 450 nm | YAG 2.7 | CASN615 | peak at 650 nm |
| Conventional two-phosphor system | 8% | 42% | 50% | — |
| Example embodiment 3 | 7% | 40% | 48% | 5% |
| Example embodiment 4 | 7% | 38% | 45% | 10% |

In example embodiments 3 and 4 in Table 7, the optical power of the green and red phosphors 71, 72 have been kept constant in comparison to the conventional two-phosphor system, while adding optical watts produced by the pulsed deep-red LED to achieve 5% and 10% optical fractions respectively, of the total optical watts of the combined spectrum.

Figure 13A:
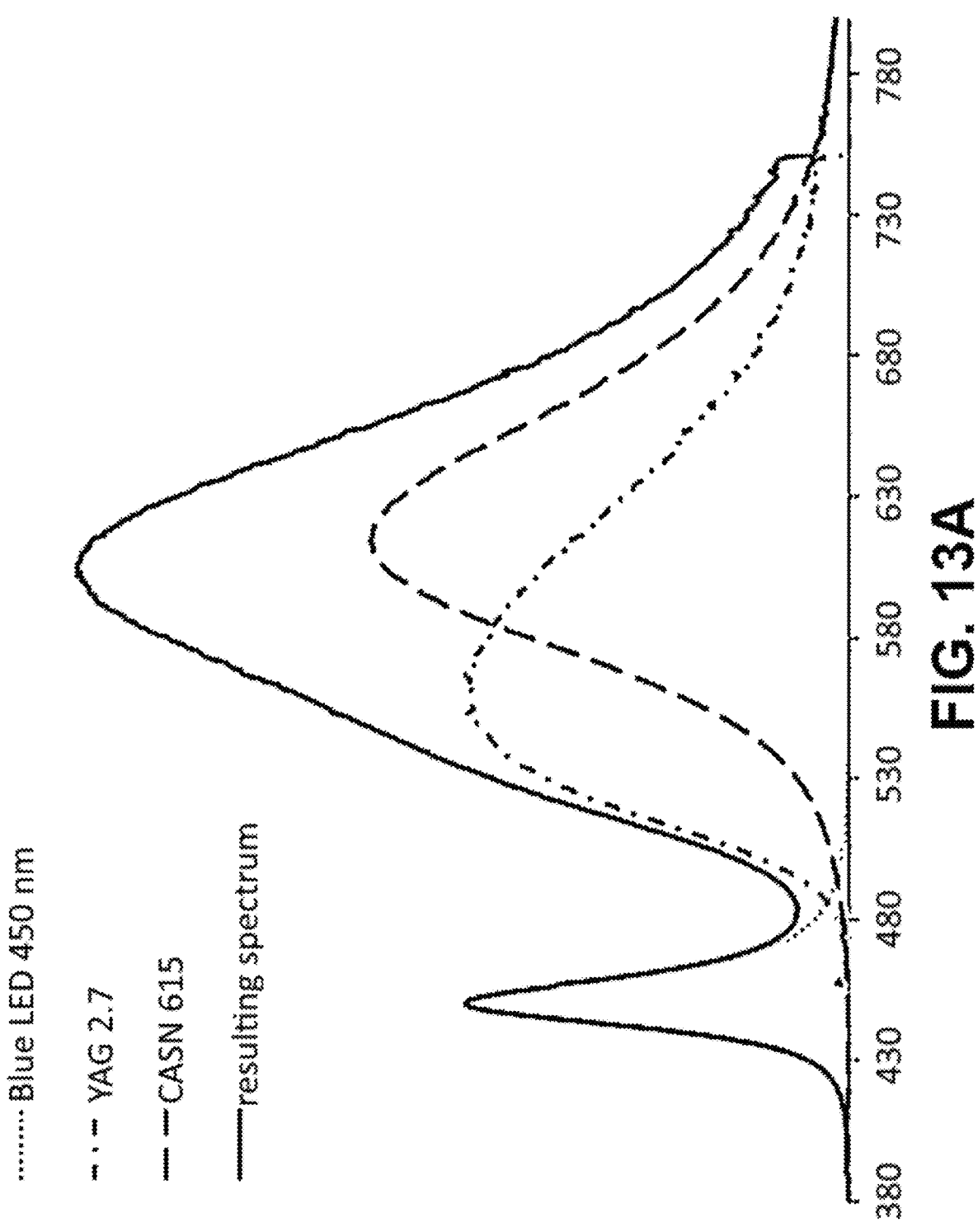
FIG. 13A is a diagram of a light spectrum of a conventional lighting arrangement including a two-phosphor system.
Figure 13B:
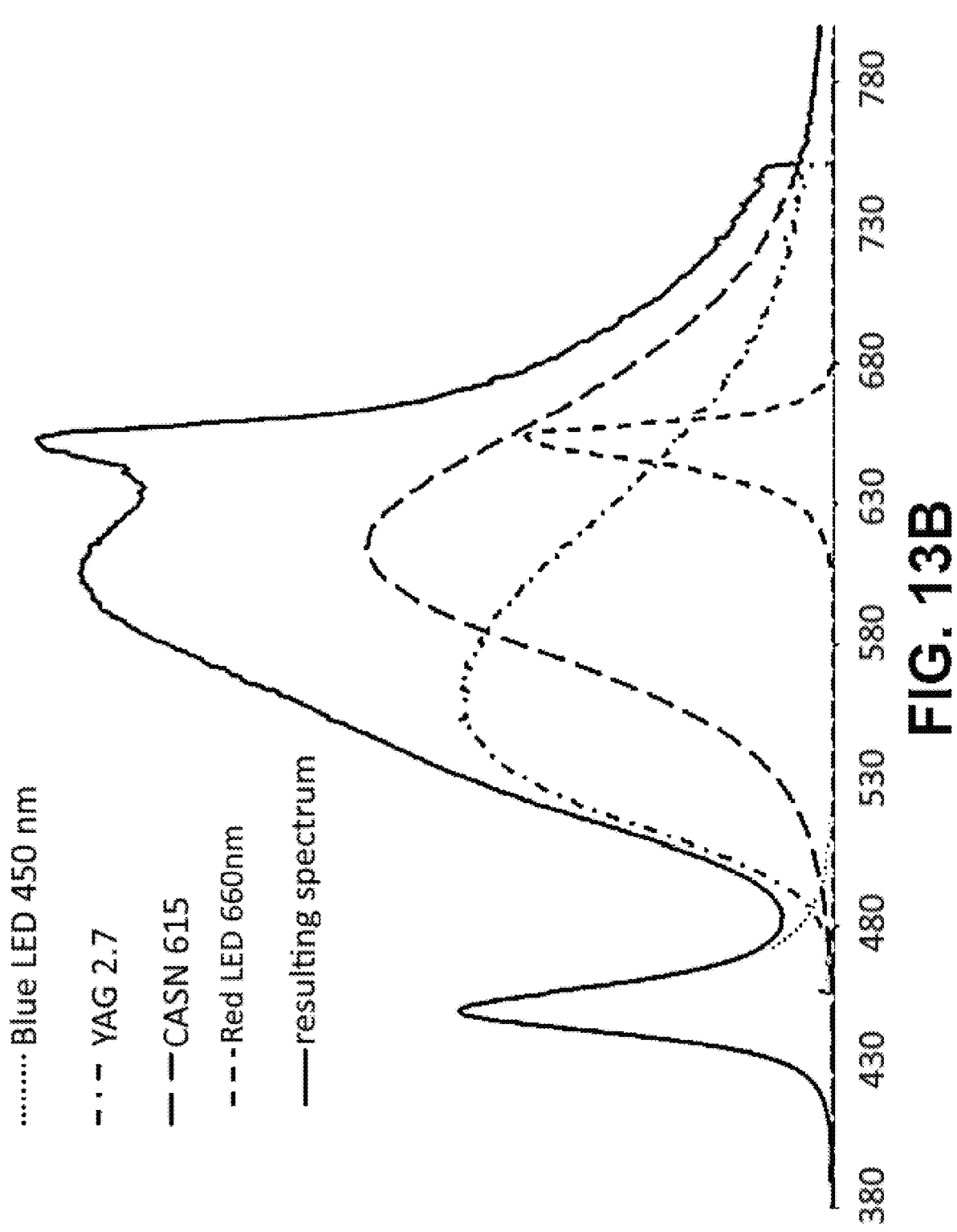
FIG. 13B is a diagram of a light spectrum of a lighting arrangement in accordance with the embodiment of FIG. 7 with a pulsed deep-red LED providing approximately 20% of the total optical watts.
Figure 13C:
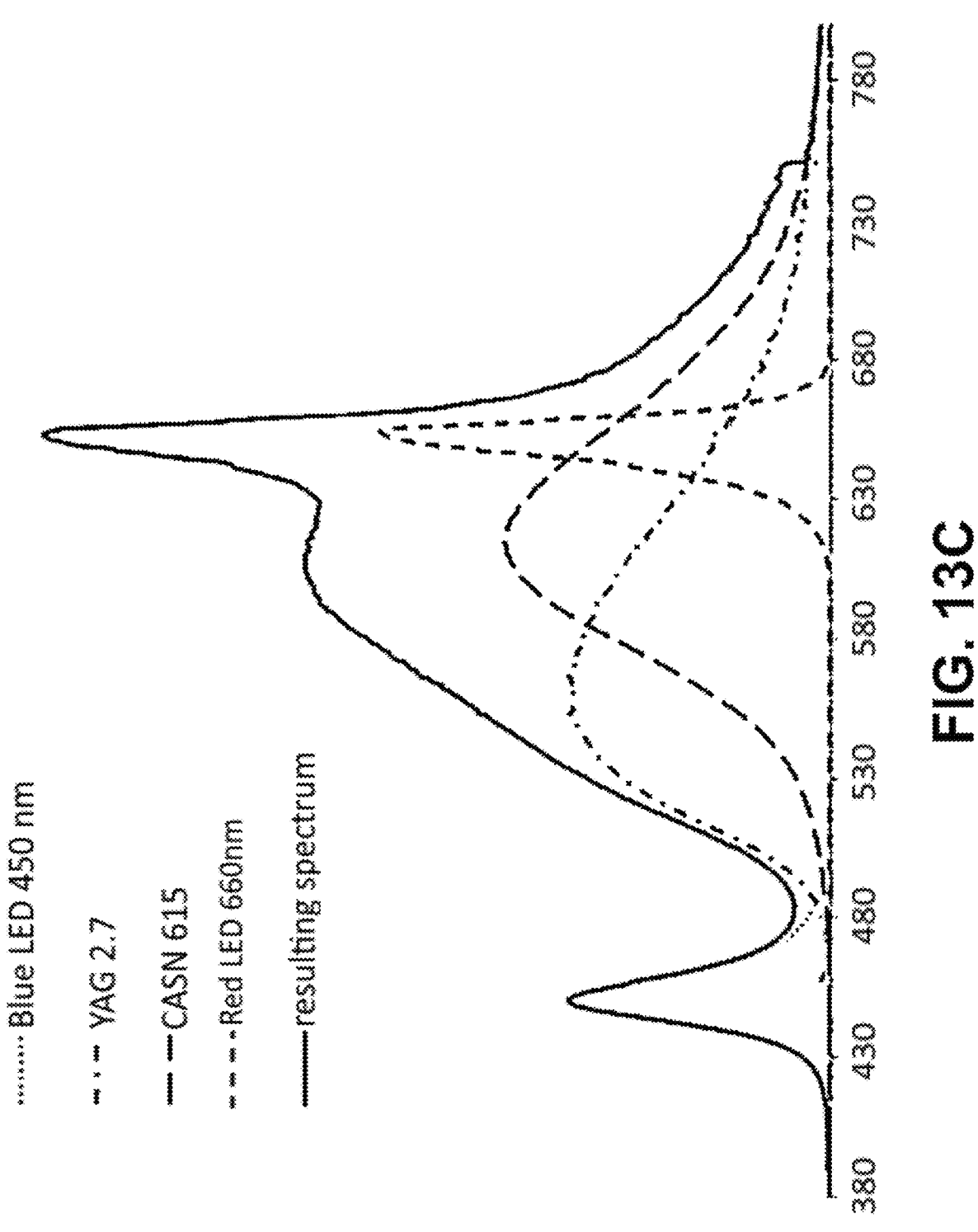
FIG. 13C is a diagram of a light spectrum of a lighting arrangement in accordance with the embodiment of FIG. 7 with a pulsed deep-red LED providing approximately 35% of the total optical watts.

A diagram of the light spectrum for the conventional two-phosphor system, example embodiment 3, and example embodiment 4 are shown in FIGS. 13A, 13B and 13C respectively. The x-axis is wavelength of the emitted light and the y-axis indicates the relative magnitude of the contributions of each component as a function of wavelength which combine to produce the total resulting light spectrum.

Figure 14A:
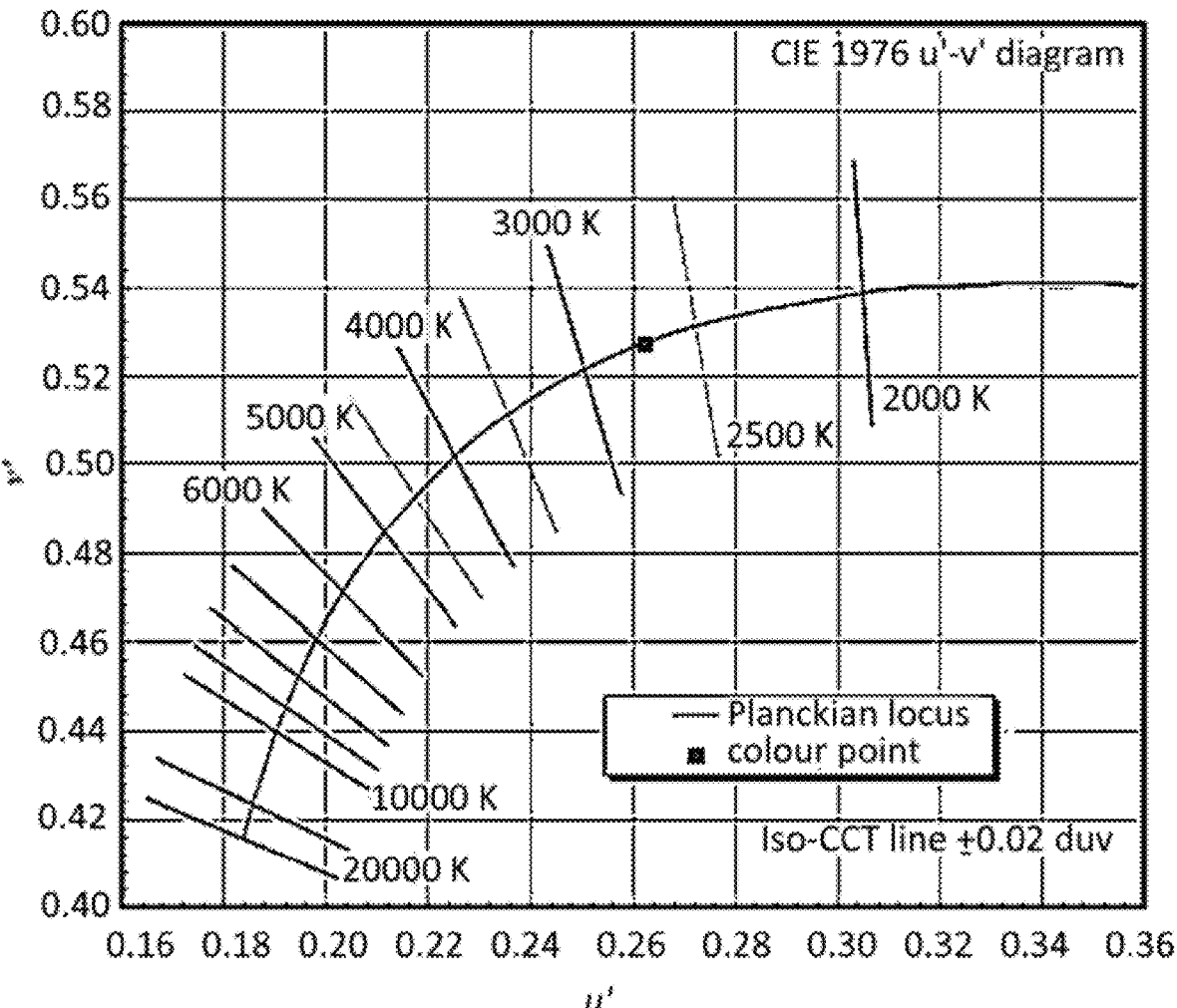
FIG. 14A is a CIE 1976 diagram showing the colour point for a conventional lighting arrangement including a two-phosphor system.
Figure 14B:
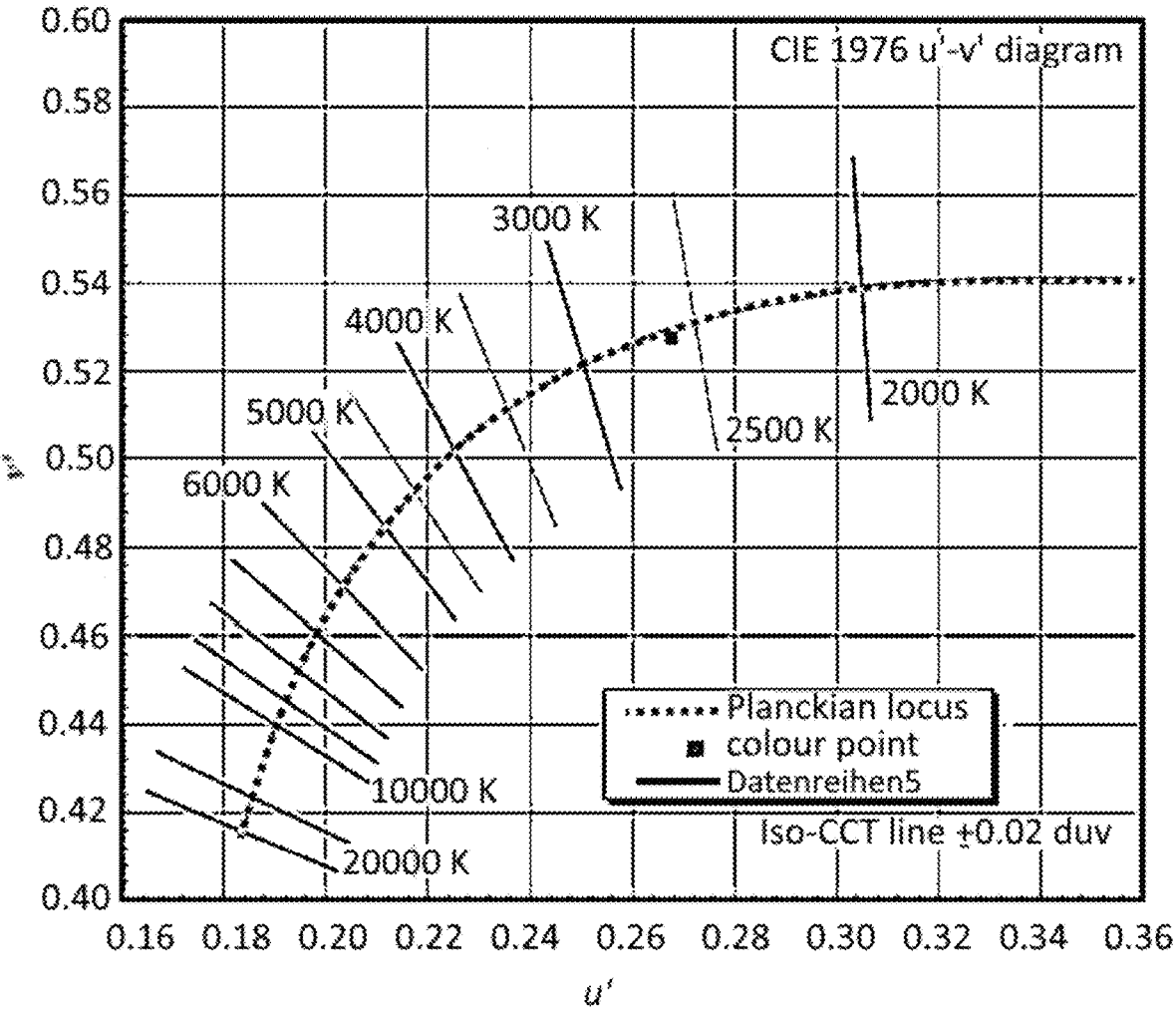
FIG. 14B is a CIE 1976 diagram showing the colour point for a lighting arrangement in accordance with the embodiment of FIG. 7 with a pulsed deep-red LED providing approximately 20% of the total optical watts.
Figure 14C:
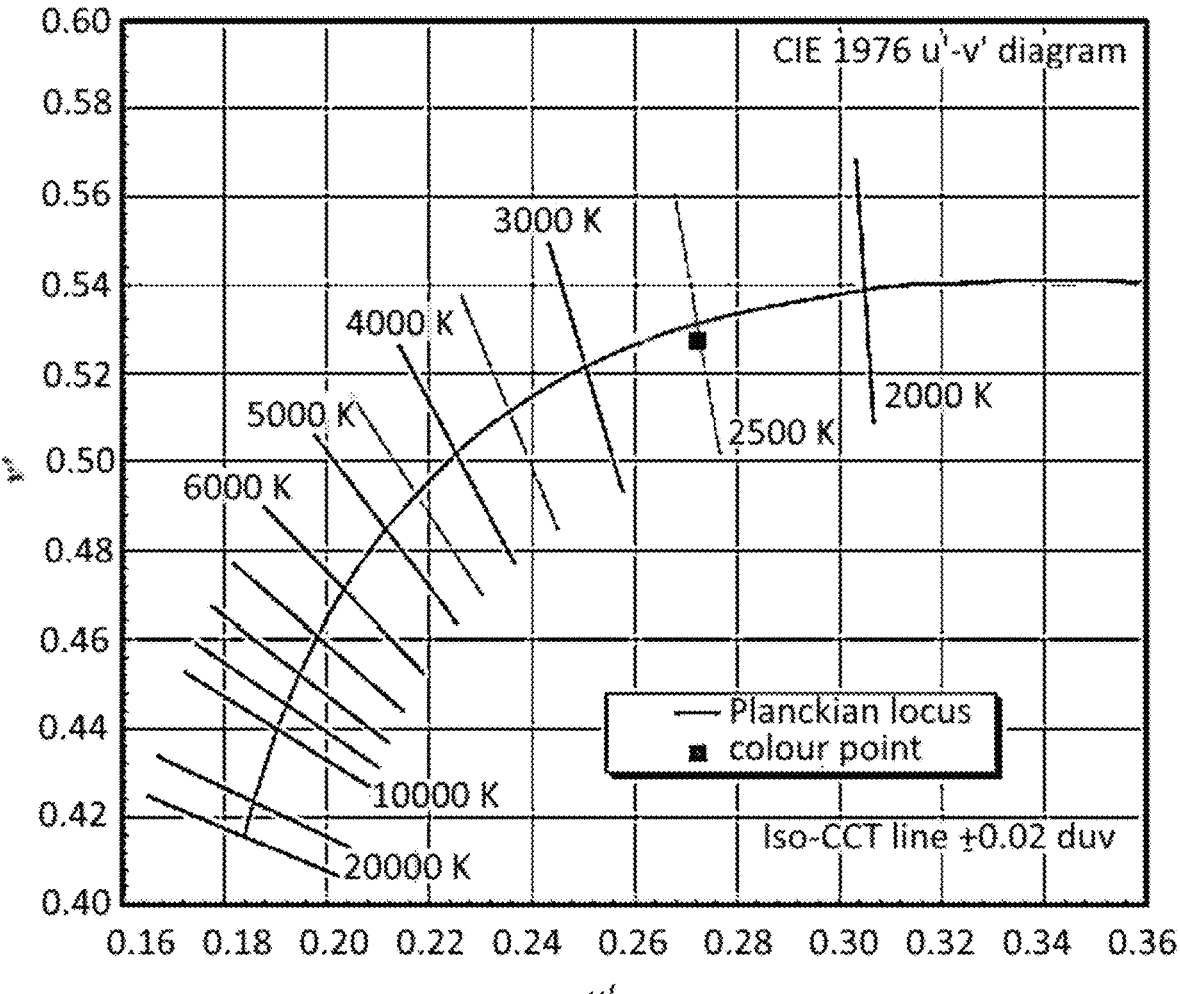
FIG. 14C is a CIE 1976 diagram showing the colour point for a lighting arrangement in accordance with the embodiment of FIG. 7 with a pulsed deep-red LED providing approximately 35% of the total optical watts.

The resulting colour point in the CIE 1976 diagram for the conventional two-phosphor system described above, for example embodiment 3, and for example embodiment 4 are shown in FIGS. 14A, 14B and 14C respectively. As can be seen, the colour points of example embodiments 3 and 4 shifts to the right into the red part of the spectrum due to the higher amount of optical watts in this part of the spectrum. The right shift of the correlated colour point in the CIE u,v diagram is mainly parallel to the black body curve, exhibiting "colour temperature dimming", due to the orientation of the black body curve in the CIE u,v diagram.

This means that the resulting, red-shifted spectrum will still appear natural due to the close location of the correlating colour point relative to the black body curve. The resulting light spectrum is therefore still applicable for general lighting application, while containing a large amount of optical watts in the deep red light spectrum which are useful for biological stimulation of human tissue.

The correlated colour temperature (CCT) and colour rendering values of the conventional two-phosphor system are shown in the two left-hand columns of Table 8 below, for example embodiment 3 in the two middle columns of Table 8, and for example embodiment 4 in the two right-hand columns of Table 8:

TABLE 8

| CCT | 2704 | CCT | 2603 | CCT | 2500 |
|---|---|---|---|---|---|
| R1 | 78.1 | R1 | 82.2 | R1 | 86.5 |
| R2 | 85.0 | R2 | 87.1 | R2 | 89.4 |
| R3 | 88.7 | R3 | 87.9 | R3 | 86.9 |
| R4 | 76.4 | R4 | 80.0 | R4 | 83.9 |
| R5 | 74.8 | R5 | 78.9 | R5 | 83.3 |
| R6 | 76.2 | R6 | 78.6 | R6 | 81.2 |
| R7 | 87.0 | R7 | 89.5 | R7 | 91.7 |
| R8 | 67.6 | R8 | 76.6 | R8 | 85.6 |
| R9 | 25.8 | R9 | 47.6 | R9 | 69.1 |
| R10 | 62.8 | R10 | 67.3 | R10 | 72.2 |
| R11 | 69.7 | R11 | 74.1 | R11 | 78.8 |
| R12 | 49.1 | R12 | 54.6 | R12 | 60.8 |
| R13 | 78.7 | R13 | 82.4 | R13 | 86.3 |
| R14 | 92.7 | R14 | 92.0 | R14 | 91.3 |
| Ra | 79.2 | Ra | 82.6 | Ra | 86.1 |

As can be seen in Table 8, the CCT values of example embodiments 3 and 4 have a reduced colour temperature compared to the conventional system. In example embodiment 3 with 5% optical fraction produced by the pulsed deep-red LED 53, the colour temperature shifts by approximately 100 Kelvin to 2603K. In example embodiment 4 with 10% optical fraction produced by the pulsed deep-red LED 53, the colour temperature shifts by approximately 200 Kelvin to 2500K. These reduced CCT values are common values which are used when dimming the colour temperature to achieve a warmer white light colour, for example to create a cosy ambient lighting referred to as "colour temperature dimming" or "warm dimming".

In some circumstances, this shift in colour temperature into the red part of the spectrum may be also used as a placebo-enhancing, desirable effect during PBM application in a therapeutic context, where the exposed person should visually notice that the amount of added PBM (via the pulsed deep-red light) has been enhanced.

In addition, example embodiments 3 and 4 have a significantly better colour rendering R9 value compared with the conventional two-phosphor system, together with an overall improvement of the colour rendering value Ra. This means that the optical perception of colours is significantly improved in example embodiments 3 and 4 compared to the conventional two-phosphor system.

In example embodiment 3 described above, the first light source 10 (the pulsed deep-red LED 53) contributes a relative optical fraction of approximately 5% of the total from the lighting arrangement. To reduce visible flicker from the first light source 10 to an acceptable level (e.g. no significant visible flicker), the pulse frequency and pulse width of the driving current 20 of the first light source 10 should be set at values which deliver the required optical power density to induce a PBM effect with sufficiently short pulses to avoid significant visible flicker.

For example embodiment 3, examples of suitable arrangements for driving the first light source 10 are shown in Table 9 below. For each driving arrangement, the pulsed driving current 20 of the first light source 10 is provided at the indicated pulse frequency, duty cycle and pulse width, and is adapted to deliver the indicated approximate peak power density during a pulse of the current at a distance to the light emitting window of the lighting arrangement where a total of 500 lux is measured.

TABLE 9

| | Frequency | Duty cycle | Pulse width | Approx. peak power density | Accumulative dose over 8 hours exposure | SVM |
|---|---|---|---|---|---|---|
| Example A | 100 Hz | 0.8% | 0.08 ms | 1 mW/cm$^2$ | 0.23 J/cm$^2$ | 0.14 |
| Example B | 200 Hz | 0.8% | 0.04 ms | 1 mW/cm$^2$ | 0.23 J/cm$^2$ | 0.1 |
| Example C | 500 Hz | 0.8% | 0.016 ms | 1 mW/cm$^2$ | 0.23 J/cm$^2$ | 0.06 |

For example embodiment 4, examples of suitable arrangements for driving the first light source 10 are shown in Table 10 below.

TABLE 10

| | Frequency | Duty cycle | Pulse width | Approx. peak power density | Accumulative dose over 8 hours exposure | SVM |
|---|---|---|---|---|---|---|
| Example A | 100 Hz | 1.6% | 0.16 ms | 1 mW/cm$^2$ | 0.46 J/cm$^2$ | 0.28 |
| Example B | 500 Hz | 1.6% | 0.03 ms | 1 mW/cm$^2$ | 0.46 J/cm$^2$ | 0.11 |
| Example C | 500 Hz | 0.8% | 0.01 ms | 2 mW/cm$^2$ | 0.46 J/cm$^2$ | 0.12 |

Note that the driving arrangement of examples B and C in Tables 9 and 10 above is less preferred, as the pulse width is very short and may be insufficient to induce significant PBM effects. On the other hand, the higher peak power density in embodiment 4 example C is beneficial for inducing PBM effects, and the lower SVM is preferable to prevent stroboscopic effects.

Pulse width and optical intensity are in general limited by the induced flicker perception, but in these driving examples it is possible to further enhance the achieved power density of the pulsed deep-red light to at least 8 mW/cm$^2$, and possibly higher, but this will result in a further red shifted light spectrum and may result perceptible flicker for persons having higher sensitivity to flicker particularly for the 100 Hz example.

Example Embodiment 5

One-Phosphor System with Pulsed Deep-Red LED(s)

In example embodiment 5 of the embodiment of FIG. 7, the pump LED 50 has a peak emission at around 450 nm, the green phosphor 51 comprises a YAG 2.7 phosphor, and the red phosphor 52 is completely absent, the red part of the spectrum being supplied by the pulsed deep-red LED with a peak emission at around 650 nm. The approximate optical fractions of these components are shown in Table 11 below for this example embodiment, compared with the optical fractions of a typical conventional two-phosphor system comprising the same components 50-52 (except the pulsed deep-red LED 53).

TABLE 11

|  | Pump LED 50 | Green phosphor 51 | Red phosphor 52 | Pulsed deep-red LED 53 |
|---|---|---|---|---|
| Example values | peak at 450 nm | YAG 2.7 | CASN615 | peak at 650 nm |
| Example embodiment 5 | 7% | 55% | — | 38% |
| Conventional two-phosphor system | 8% | 42% | 50% | — |

In example embodiment 5, the optical power of the red phosphor 52 is eliminated in comparison to the conventional system, to allow adding optical watts in the red spectrum by the pulsed deep-red LED, while keeping a similar colour point and correlated colour temperature (CCT) compared with the conventional system. Such a system could be beneficial in two ways: 1) it allows for the use of simpler LEDs with just one green phosphor 51 which brings manufacturing and cost benefits and 2) it allows for a significant increase in optical fraction from the pulsed deep-red LED, which allows for a higher daily dose while keeping the colour point and CCT similar to the conventional two-phosphor system.

Figure 15A:
FIG. 15A is a diagram of a light spectrum of a lighting arrangement in accordance with the embodiment of FIG. 7 with a pulsed deep-red LED providing substantially all light in the red part of the spectrum.
Figure 15B:
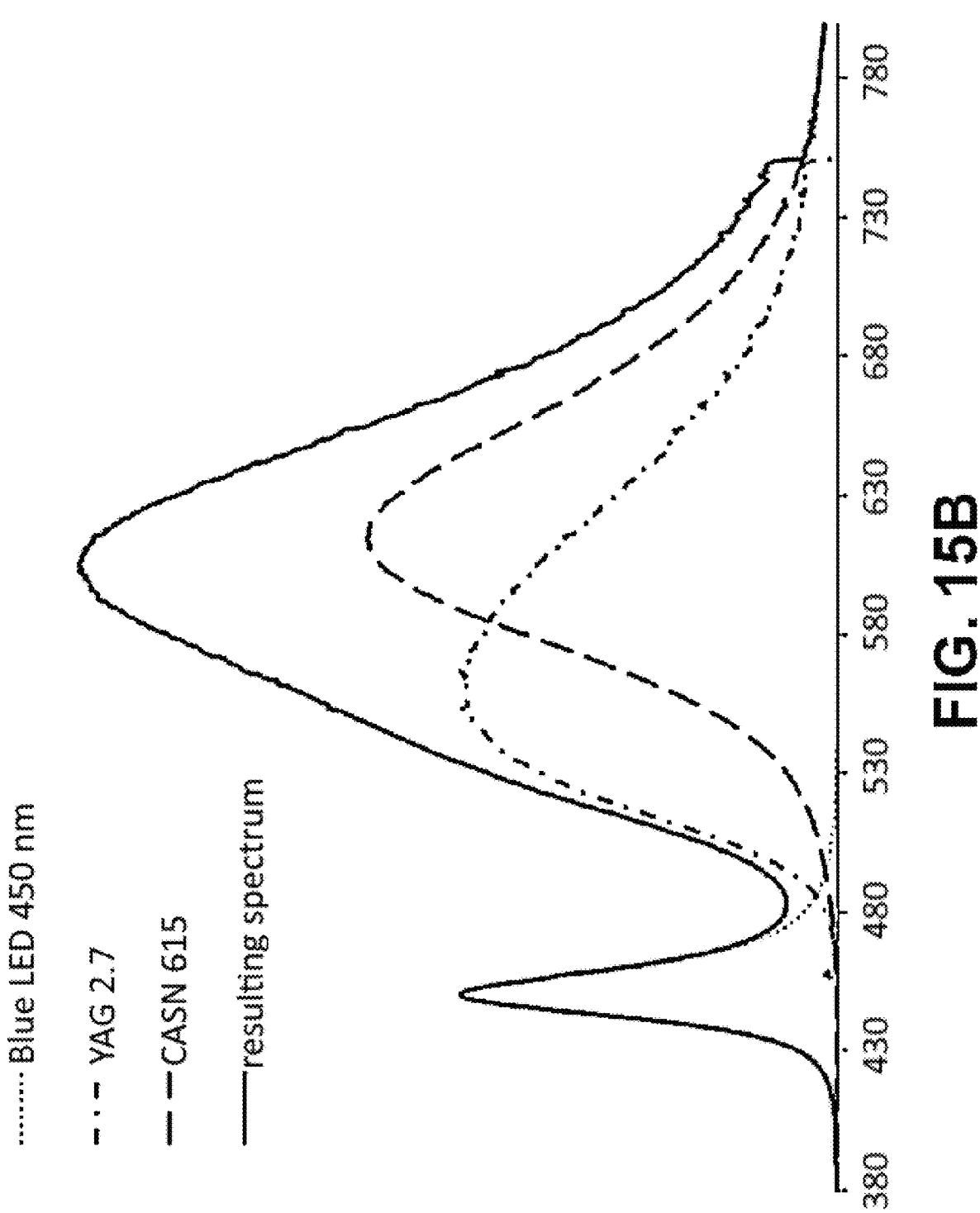
FIG. 15B is a diagram of a light spectrum of a conventional lighting arrangement including a two-phosphor system.

A diagram of the light spectrum for example embodiment 5 and for the conventional two-phosphor system described above are shown in FIGS. 15A and 15B respectively. The x-axis is wavelength of the emitted light and the y-axis indicates the relative magnitude of the contributions of each component as a function of wavelength which combine to produce the total resulting light spectrum.

Figure 16A:
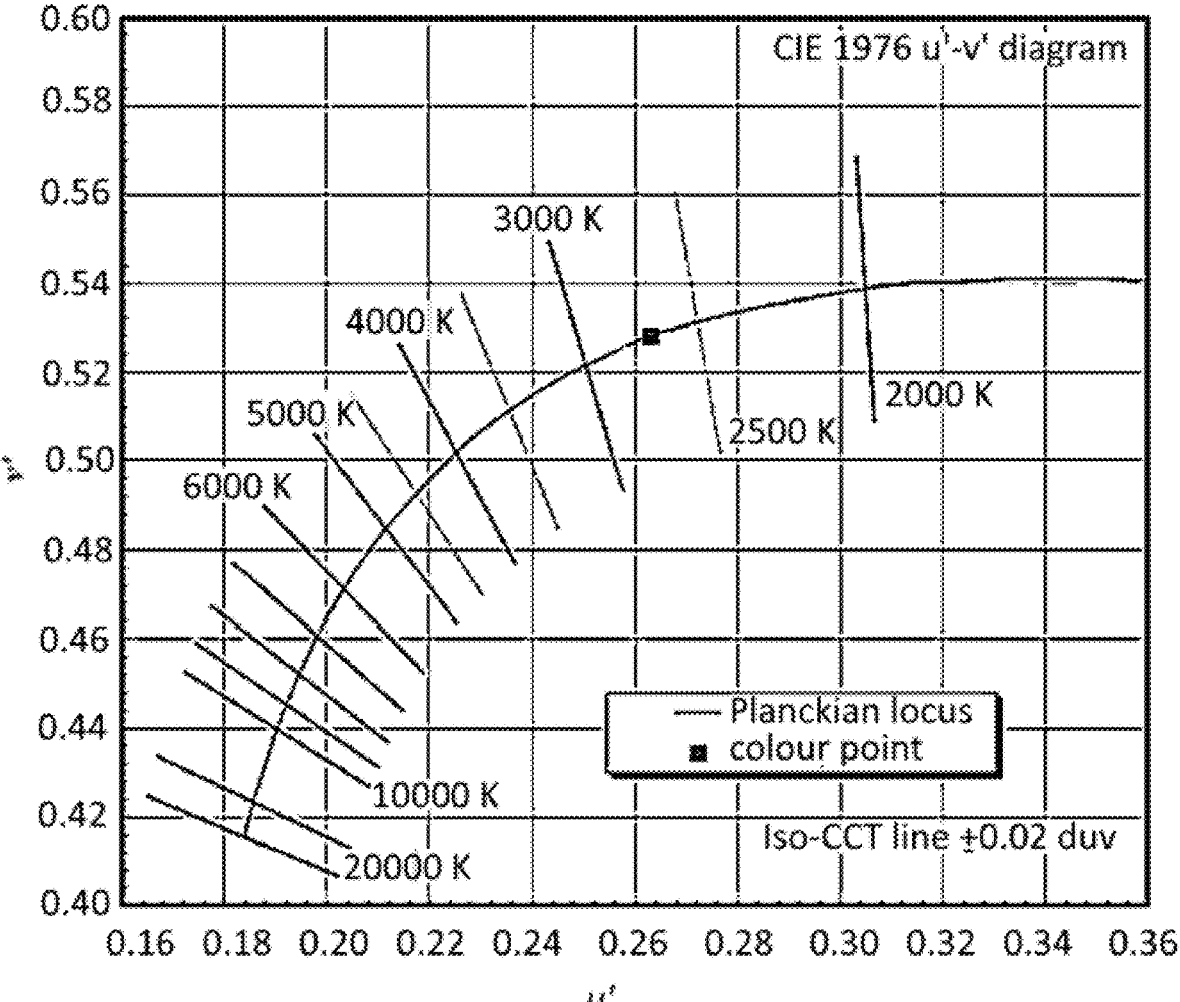
FIG. 16A is a CIE 1976 diagram showing the colour point for a lighting arrangement in accordance with the embodiment of FIG. 7 with a pulsed deep-red LED providing substantially all light in the red part of the spectrum.
Figure 16B:
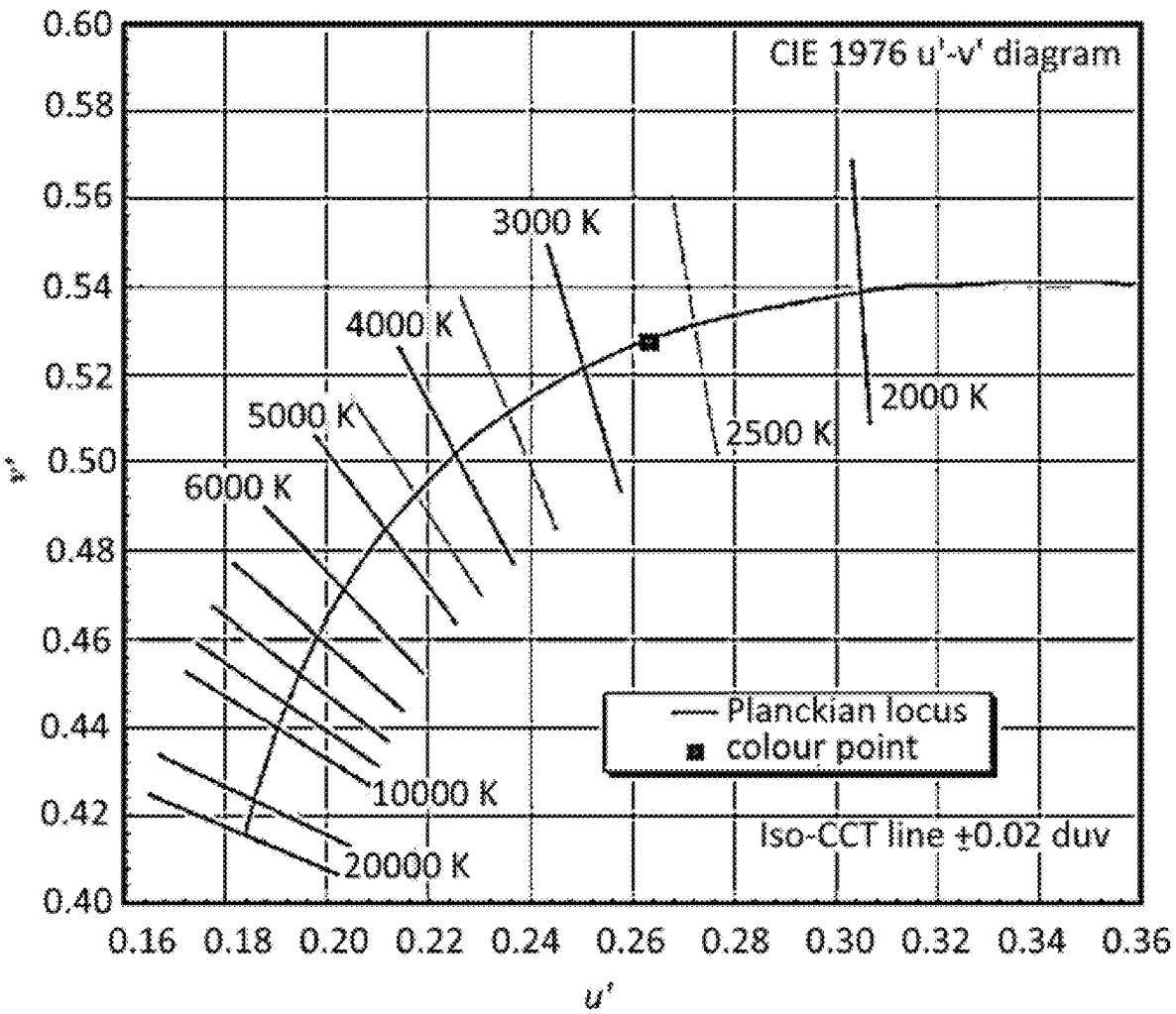
FIG. 16B is a CIE 1976 diagram showing the colour point for a conventional lighting arrangement including a two-phosphor system.

The resulting colour point in the CIE 1976 diagram for example embodiment 5 and for the conventional system are shown in FIGS. 16A and 16B respectively. As can be seen, the colour point of the two systems is almost identical.

The correlated colour temperature (CCT) and colour rendering values of example embodiment 1 are shown in the two left-hand columns of Table 2 below, and for the conventional system are shown in the two right-hand columns of Table 12:

TABLE 12

| CCT | 2702 | CCT | 2704 |
|---|---|---|---|
| R1 | 94.1 | R1 | 78.1 |
| R2 | 93.0 | R2 | 85.0 |

28

TABLE 12-continued

| CCT | 2702 | CCT | 2704 |
|---|---|---|---|
| R3 | 69.2 | R3 | 88.7 |
| R4 | 86.7 | R4 | 76.4 |
| R5 | 96.8 | R5 | 74.8 |
| R6 | 80.7 | R6 | 76.2 |
| R7 | 75.4 | R7 | 87.0 |
| R8 | 56.9 | R8 | 67.6 |
| R9 | 20.3 | R9 | 25.8 |
| R10 | 78.5 | R10 | 62.8 |
| R11 | 88.7 | R11 | 69.7 |
| R12 | 64.8 | R12 | 49.1 |
| R13 | 97.9 | R13 | 78.7 |
| R14 | 81.0 | R14 | 92.7 |
| Ra | 81.6 | Ra | 79.2 |

As can be seen in Table 12, the CCT values are very similar for the two systems, indicating that the light from the two systems will be difficult to be distinguish visually from each other. However, the spectrum of the lighting arrangement with pulsed deep red LED has slightly better colour rendering, compared with the conventional system, so that the optical perception of colours is improved compared to the conventional system.

In example embodiment 5 described above, the first light source 10 (the pulsed deep-red LED 53) contributes a relative optical fraction of approximately 38% of the total, average optical power from the lighting arrangement. To reduce visible flicker from the first light source 10 to an acceptable level (e.g. no significant visible flicker), the pulse frequency and pulse width of the driving current 20 of the first light source 10 should be set at values which deliver the required optical power to induce a PBM effect with sufficiently short pulses to avoid significant visible flicker.

For example embodiment 5, examples of suitable arrangements for driving the first light source 10 are shown in Table 13 below. For each driving arrangement, the pulsed driving current 20 of the first light source 10 is provided at the indicated pulse frequency, duty cycle and pulse width, and is adapted to deliver the indicated approximate peak power density during a pulse of the current at a distance to the light emitting window of the lighting arrangement where a total of 500 lux is measured.

TABLE 13

|  | Frequency | Duty cycle | Pulse width | Approx. Peak power density | Accumulative dose over 8 hours exposure | SVM |
|---|---|---|---|---|---|---|
| Example A | 100 Hz | 1.6% | 0.15 ms | 4 mW/cm$^2$ | 1.8 J/cm$^2$ | 1.34 |
| Example B | 500 Hz | 1.6% | 0.03 ms | 4 mW/cm$^2$ | 1.8 J/cm$^2$ | 0.52 |

Note that example B shown above is less preferred, as the pulse width is very short and may be insufficient to induce significant PBM effects. However, further increasing the frequency does improve the SVM results. An increase in pulse width, and increase in optical intensity, of the first light source 10 is limited to avoid significant visible flicker. Furthermore, an increase in pulse width will increase the relative optical fraction of the red light in comparison to the total spectrum, moving the colour point of the combined light from the lighting arrangement.

The above described driving arrangements can also be applied in a similar fashion on other phosphor systems.

In sum, the present disclosure provides at least a lighting arrangement, a lighting method, and a lamp for general lighting, a retrofit light bulb for general lighting, a retrofit light tube for general lighting and a luminaire for general lighting. By sophisticated pulsing of the red light source, an appropriate and beneficial amount of radiation in a predetermined spectrum may be provided at a reasonable amount of power consumption. Combining such pulsed red light source into a general lighting apparatus may greatly expand it use and may turn it into a general lighting source with health benefits that is easy to use. Pulsing the red light source may also help prevent overdosage if the user is exposed to radiation in the predetermined spectrum for an extended period of time, such as more than 60 minutes.

The descriptions above are intended to be illustrative, not limiting. It will be apparent to the person skilled in the art that alternative and equivalent embodiments of the invention can be conceived and reduced to practice, without departing from the scope of the claims set out below.

The invention claimed is:

1. A lighting arrangement for general lighting, comprising:

a first red light source operable to emit a first light that is substantially red light, having a peak emission wavelength in a range from 615 nm to 690 nm;

one or more driver circuits operable to provide a first pulsed driving current to the first light source for producing the first light pulsing with a first peak radiant power;

a second light source operable to emit a second light, the second light source being operable to emit at least 250 lumens;

wherein the lighting arrangement is operable to form a combined light that is substantially white light, from the first light and second light;

wherein the first peak radiant power enables a received power density in a range 0.4-50 mW/cm², measured at a common average distance of between 0.2 m and 5 m from the lighting arrangement or at a distance from the lighting arrangement where the combined light has an illuminance of approximately 500 Lux; and wherein a first radiant power of the first light is at least twice a second radiant power of the second light during the pulses of the first driving current.

2. The lighting arrangement of claim 1, wherein the one or more driver circuits is operable to provide a second driving current to the second light source but not to the first light source, wherein the second driving current is a DC current, an AC current, a rectified AC current, or a pulsed current having a pulse frequency of 2 kHz or more.

3. The lighting arrangement of claim 1, wherein an average first radiant power of the first light over a time interval is 40% or less of a sum of the average first radiant power of the first light and an average second radiant power of the second light over the time interval.

4. The lighting arrangement of claim 1, wherein the first light source has a peak radiant power in a range from 645 nm to 675 nm.

5. The lighting arrangement of claim 1, wherein the second light source comprises a multi-phosphor system having a plurality of phosphors of different emission wavelengths.

6. The lighting arrangement of claim 1, wherein a peak emission power of the first light source enables a received power density in a range 1-15 mW/cm², wherein the peak emission power is measured at a common average distance of between 0.2 m and 5 m from the lighting arrangement, or is measured at a distance from the lighting arrangement where the illuminance of the combined light from the first and second light sources is approximately 500 Lux.

7. The lighting arrangement of claim 1, wherein the first light source emits at least 3,000 J within 8 hours.

8. The lighting arrangement of claim 1, wherein the first light source is operable to deliver a daily dosage (energy per unit area) that is sufficient to induce PBM response in a human body, wherein the dosage is measured at a common average distance of between 0.2 m and 5 m from the lighting arrangement, or is measured at a distance from the lighting arrangement where the illuminance of the combined light from the first and second light sources is approximately 500 Lux.

9. The lighting arrangement of claim 1, wherein the first light source is operable to deliver a daily dosage of 0.01-10 J/cm², wherein the daily dosage is measured at a common average distance of between 0.2 m and 5 m from the lighting arrangement; or is measured 30 at a distance where the illuminance of the combined light from the first and second lights sources is approximately 500 Lux.

10. The lighting arrangement of claim 1, wherein pulse characteristics of the first light are such that the combined light generated by the first and second light sources together has a luminous flux having a Percent Flicker of not more than 40%, during steady-state operation of the lighting arrangement.

11. The lighting arrangement of claim 1, wherein pulse characteristics of the first light are such that the combined light generated by the first and second light sources together has a short term flicker indicator ($P_{st}LM$) of not more than 1, during steady-state operation of the lighting arrangement.

12. The lighting arrangement of claim 1, wherein pulse characteristics of the first light are such that the combined light generated by the first and second light sources together has a Stroboscopic Visibility Measure of not more than 0.4, during steady-state operation of the lighting arrangement.

13. The lighting arrangement of claim 1, wherein pulse characteristics of the first light are such that no stroboscopic effects can be observed by the human eye in the combined light from the first and second light sources during steady-state operation of the lighting arrangement.

14. The lighting arrangement of claim 1, wherein the combined light from the first and second light sources has a correlated color temperature in the range 1700-6500K.

15. The lighting arrangement of claim 1, wherein the combined light from the first and second light sources has a color rendering index in the range 80-100 at a correlated color temperature of about 2700K.

16. The lighting arrangement of claim 1, wherein the lighting arrangement is suitable for task lighting.

* * * * *